US006235474B1

(12) United States Patent
Feinberg

(10) Patent No.: US 6,235,474 B1
(45) Date of Patent: *May 22, 2001

(54) METHODS AND KITS FOR DIAGNOSING AND DETERMINATION OF THE PREDISPOSITION FOR DISEASES

(75) Inventor: Andrew P. Feinberg, Lutherville, MD (US)

(73) Assignee: The Johns Hopkins University, Baltimore, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/114,825

(22) Filed: Jul. 14, 1998

Related U.S. Application Data

(63) Continuation-in-part of application No. 08/995,150, filed as application No. PCT/US97/23991 on Dec. 29, 1997, now abandoned.
(60) Provisional application No. 60/034,095, filed on Dec. 30, 1996, now abandoned.

(51) Int. Cl.[7] .............................. C12Q 1/68; C12P 19/34; C07H 21/02; C07H 21/04
(52) U.S. Cl. ........................... 435/6; 435/91.2; 536/23.1; 536/24.31; 536/24.33
(58) Field of Search ..................... 435/6, 91.2; 536/23.1, 536/24.31, 24.33

(56) References Cited

U.S. PATENT DOCUMENTS 5,709,998 * 1/1998 Kinzler et al. ........................... 435/6
5,871,917 2/1999 Duffy .

OTHER PUBLICATIONS

Mori et al., "Relaxation of insulin–like growth factor 2 gene imprinting in esophageal cancer", International Journal of Cancer, vol. 68, pp. 441–446, Aug. 1996.*
Spencer et al., "Failure of imprinting at IGF2: Two models of mutation–selection balance", American Journal of Genetics, vol. 56, pp. 434–437, Nov. 1994.*
Dallapiccola et al., "From genetic research into clinical practice", Acta Geneticae Medicae et Gemellologiae, vol. 46(3), pp. 139–146, 1997.*
Imprinting mutations in the Beckwith–Wiedemann syndrome suggested by an altered imprinting pattern in the IGF2–H19 domain, 1995 Oxford University Press, Human Molecular Genetics, 1995, vol. 4, No. 12, pp 2379–2385.
Aaltonen, Lauri A., et al., "Incidence of Hereditary Nonpolyposis Colorectal Cancer and the Feasibility of Molecular Screening for the Disease", *The New England Journal of Medicine,* vol. 338, No. 21, pp. 1481–1486, (1988).

(List continued on next page.)

*Primary Examiner*—Jeffrey Fredman
*Assistant Examiner*—Arun Kr. Chakrabarti
(74) *Attorney, Agent, or Firm*—Kilpatrick Stockton LLP

(57) ABSTRACT

The present invention provides a method and a kit for the purpose of diagnosing a disease or determining the predisposition for a disease by measuring abnormalities in imprinting of a gene or population of genes. The disease that can be diagnosed by the present invention is selected from any disease that is mediated by, or is associated with, a particular gene or combination of genes that are subject to imprinting. According the present invention, the imprinting can be abnormally on or can be abnormally off. In those cases where the particular gene that is being examined is normally imprinted, but in the disease state is abnormally not imprinted, the present invention is designed to detect the "loss of imprinting" (hereinafter "LOI") thereby indicating that the disease may be present.

20 Claims, 6 Drawing Sheets

OTHER PUBLICATIONS

Adam, Gail I., et al., "Allele–specific in situ hybridization (ASISH) analysis: a novel technique which resolves differential allelic usage of H19 within the same cell lineage during human placental development", *Development*, vol. 122(3), pp. 839–847, (1996).

Allen, Nicholas D., et al., "Epigenetic Control of Transgene Expression and Imprinting by Genotype–Specific Modifiers", *Cell*, vol. 61, pp. 853–861, (1990).

Aparicio, Oscar M., "Modifiers of Position Effect are Shared between Telomeric and Silent Mating–Type Loci in *S. cerevisiae*", *Cell*, vol. 66, pp. 1279–1287, (1991).

Barletta, J.M., et al., "Reversal of loss of imprinting in tumor cells by 5–aza–2'–deoxycytidine", *Cancer Research*, vol. 57, No. 1, pp. 48–50, (1997).

Barlow, D.P., et al., "The mouse insulin–like growth factor type–2 receptor is imprinted and closely linked to the Tme locus", *Nature*, vol. 349, pp. 84–87, (1991).

Bartolomei, Marisa S., "Epigenetic mechanisms underlying the imprinting of the mouse H19 gene", *Genes and Development*, vol. 7, No. 9, pp. 1663–1673, (1993).

Brachmann, Carrie Baker, et al., "The SIR2 gene family, conserved from bacteria to humans, functions in silencing, cell cycle progression, and chromosome stability", *Genes and Development*, vol. 9, pp. 2888–2902, (1995).

Brassett, Cecilia, et al., "Microsatellite instability in early onset and familial colorectal cancer", *Journal of Medical Genetics*, vol. 33, pp. 981–985, (1996), (Abstract only).

Brownell, James E., et al., "Tetrahymena Histone Acetyltransferase A: A Homolog to Yeast Gcn5p Linking Histone Acetylation to Gene Activation", *Cell*, vol. 84, pp. 843–851, (1996).

Bubb, Vivien J., "Microsatellite instability and the role of hMSH2 in sporadic colorectal cancer", *Oncogene*, vol. 12, pp. 2641–2649, (1996).

Buck, Stephen W., et al., "Action of a RAP1 carboxy–terminal silencing domain reveals an underlying competition between HMR and telomeres in yeast", *Genes & Development*, vol. 9, pp. 370–384, (1995).

Caron, Huib, et al., "Evidence for two tumour suppressor loci on chromosomal bands 1p35–36 involved in neuroblastoma: one probably imprinted, another associated with N–myc amplification", *Human Molecular Genetics*, vol. 4, No. 4, pp. 535–539, (1995).

Caron, Huib et al., "Allelic loss of chromosome 1p36 in neuroblastoma is of preferential maternal origin and correlates with N–myc amplification", Nature Genet., vol. 4, pp. 187–189, (Jun., 1993).

de Capoa, A., et al., "Computer–Assisted Analysis of Methylation Status of Individual Interphase Nuclei in Human Cultured Cells", *Cytometry*, (1998), vol. 31, pp. 85–92.

DeChiara, Thomas M., et al., "Parental Imprinting of the Mouse Insulin–like Growth Factor II Gene", *Cell*, vol. 64, pp. 849–859, (1991).

Dietmaier, Wolfgang, et al., "Diagnostic Microsatellite Instability: Definition and Correlation with Mismatch Repair Protein Expression", *Cancer Research*, vol. 57, No. 21, pp. 4667–5472, (1997).

Deng, Guoren, et al., "Loss of Heterozygosity in Normal Tissue Adjacent to Breast Carcinomas", *Science*, vol. 274, pp. 2057–2059, (1996).

Dittrich, B., et al., "Imprint switching on human chromosome 15 may involve alternative transcripts of the SNRPN gene", *Nat. Genet.*, vol. 14, pp. 163–170, (1996).

Douc–Rasy, S., et al., "High Incidence of loss of heterozygosity and abnormal imprinting of H19 and IGF2 genes in invasive cervical carcinomas: Uncoupling of H19 and IGF2 expression and biallelic hypomethylation of H19", *Oncogene*, vol. 12, pp. 423–430, (1996).

Feinberg, Andrew P., et al., "Hypomethylation distinguishes genes of some human cancers from their normal counterparts", *Nature*, vol. 301, pp. 89–92, (1983).

Feinberg, A.P., et al., "Loss of Imprinting in Human Cancer", (1994), Cold Spring Harbor Symposia on Quantitative Biology, vol. LIX, pp. 357–364.

Feinberg, Andrew P., et al., "Reduced Genomic 5–Methylcytosine Content in Human Colonic Neoplasia", (1988), *Cancer Research*, vol. 48, pp. 1159–1161.

Feinberg, Andrew P., "Genomic Imprinting and gene activation in cancer", *Nature Genetics*, vol. 4, pp. 110–113, (1993).

Feinberg, Andrew P., et al., "Genomic Imprinting, DNA Methylation, and Cancer", (1995), *Journal of the National Cancer Institute Monographs*, vol. 17, pp. 21–26.

Feinberg, A. P., "Alterations in DNA methylation in colorectal polyps and cancer", *Prog. Clin. Biol. Res.* 279:309–317, (1988).

Ferguson–Smith, Anne C., et al., "Parental–origin–specific epigenetic modification of the mouse H19 gene", *Nature*, vol. 362, pp. 751–755, (1993).

Ferguson–Smith, Anne C., et al., "Embryological and molecular investigations of parental imprinting on mouse chromosome 7", *Nature*, vol. 351, pp. 667–665, (Jun., 1991).

Ford, D. et al., "Estimates of the Gene Frequency of BRCA1 and its Contribution to Breast and Ovarian Cancer Incidence", *Am. J. Hum. Genet.*, vol. 57, pp1457–1461, (1995).

Giannoukakas, Nick, "Parental genomic imprinting of the human IGF2 gene", *Nat. Genet.*, vol. 4, pp. 98–101, (1993).

Goelz, Susan E., et al., "Hypomethylation of DNA from Benign and Malignant Human Colon Neoplasm", *Science*, vol. 228, pp. 187–190, (1985).

Hashimoto, Kazumasa et al., "Loss of imprinting in choriocarcinoma", *Nature Genetics*, vol. 9, pp. 109–110, (1995).

He, Liangme et al., "Hypervariable allelic expression patterns of the imprinted IGF2 gene in tumor cells", *Oncogene*, vol. 16, pp. 113–119, (1998).

Henry, I., et al., "Uniparental paternal disomy in a genetic cancer–predisposing syndrome", *Nature*, vol. 35 pp. 609–610, (1991).

Herman, James G. et al., "Incidence and functional consequences of hMLH1 promoter hypermethylation in colorectal carcinoma", *Proceedings of the National Academy of Sciences USA*, vol. 95, pp. 6870–6875, (1998).

Heutink, Peter et al., "Further Localization of the Gene for Hereditary Paragangliomas and Evidence for Linkage in Unrelated Families", *European Journal of Human Genetics*, vol. 2, pp. 148–158, (1994).

Hibi, Kenji et al., "Loss of H19 Imprinting in Esophageal Cancer", *Cancer Research*, vol. 56, pp. 429–661, (1996).

Hoovers, Jan M. N., et al., "Multiple genetic loci within 11p15 defined by Beckwith–Wiedemann syndrome rearrangement breakpoints and subchromosomal transferable fragments", *Proceedings of the National Academy of Sciences USA*, vol. 92, pp. 12456–12460, (1995).

Issa, Jean–Pierre J., et al., "Switch from monoallelic to biallelic human IGF2 promoter methylation during aging and carcinogenesis", *Proceedings of the National Academy of Sciences USA,* vol. 93, pp. 11757–11762, (1996).

Jarrard, David F., et al., "Regional Loss of Imprinting of the Insulin–like Growth Factor II Gene Occurs in Human Prostate Tissues", *Clinical Cancer Research,* vol. 1, No. 12, pp. 1439–1661, (1995).

Jones, Peter A., et al., "The Role of DNA Methylation in Cancer", *Advances in Cancer Research,* vol. 54, pp. 1–23, (1990).

Kim, Hoguen, et al., "Clinical and Pathological Characteristics of Sporadic Colorectal Carcinomas with DNA Replication Errors in Microsatellite Sequences", *American Journal of Pathology,* vol. 145, No. 1, pp. 148–156, (1994).

Kitsberg, D., et al., "Allele–specific replication timing of imprinted gene regions", *Nature,* vol. 364, pp. 459–463, (1993).

Knoll, J.H.M., et al., "Angelman Syndrome: Three Molecular Classes Identified with Chromosome 15q11q13–specific DNA Markers", *The American Journal of Human Genetics,* vol. 47, pp. 149–155, (1990).

Kondo, Masashi, et al., "Frequent loss of imprinting of the H19 gene is often associated with its expression in human lung cancers", *Oncogene,* vol. 10, pp. 1193–1198, (1995).

Kuroiwa, Yoshima, et al., "Peg3 imprinted gene on proximal chromosome 7 encodes for a zinc finger protein", *Nature Genetics,* vol. 12, pp. 186–190, (1996).

Koufos, Alex, et al., "Familial Wiedemann–Beckwith Syndrome and a Second Wilms Tumor Locus Both Map to 11p15.5", *Am. J. Hum. Genet.,* vol. 44, pp. 711–719, (1989).

LaSalle, Janine M., "Homologous Association of Oppositely Imprinted Chromosomal Domains", *Science,* vol. 272, pp. 725–728, (1996).

Ledbetter, David H., "Uniparental disomy in humans: development of an imprinting map and its implications for prenatal diagnosis", *Human Molecular Genetics,* vol. 4, pp. 1757–1764, (1995).

Lee, Mong–Hong, et al., "Cloning of p57$^{KIP2}$, a cyclin–dependent kinase inhibitor with unique domain structure and tissue distribution", *Genes & Development,* vol. 9, pp. 639–649, (1995).

Lee, Maxwell P., et al., "Human KVLQT1 gene shows tissue–specific imprinting and encompasses Beckwith–Wiedemann syndrome chromosomal rearrangements", *Nature Genetics,* vol. 15, pp. 181–185, (1997).

Li, En, et al., "Role for DNA methylation in genomic imprinting", *Nature,* vol. 366, pp. 362–365, (1993).

Li, Xuri, et al., "Expression, promoter usage and parental imprinting status of insulin–like growth factor II (IGF2) in human hepatoblastoma: uncoupling of IGF2 and H19 imprinting", *Oncogene,* vol. 11, pp. 221–229, (1995).

Liu, Bo, et al., "Mismatch repair gene defects in sporadic colorectal cancers with microsatellite instability", *Nature Genetics,* vol. 9, pop. 48–55, (1995).

Lukish, J.R., et al., "Prognostic Significance of DNA Replication Errors in Young Patients with Colorectal Cancer", *Annals of Surgery,* vol. 227(1), pp. 51–56, (1988), (Abstract only).

Lynch, Henry T., et al., "Identifying Hereditary Nonpolyposis Colorectal Cancer", *The New England Journal of Medicine,* vol. 338, pp. 1537–1538, (1988).

Matsuoka, Shuhei, et al., "p57$^{KIP2}$, a structurally distinct member of the p21$^{CIP1}$ Cdk inhibitor family, is a candidate tumor suppressor gene", *Genes & Development,* vol. 9, pp. 650–662, (1995).

Matsuoka, Shuhei, et al., "Imprinting of the gene encoding a human cyclin–dependent kinase inhibitor, p57KIP2, on chromosome 11p15", *Proc. Natl. Acad. Sci. USA,* vol. 93, pp. 3026–3030, (1996).

Mattei, M. G., et al., "Chromosome 15 anomalies and the Prader–Willi syndrome: Cytogenetic analysis", *Human Genetics,* vol. 66, pp. 313–334, (1984).

Moulton, Thomas, et al., "Epigenetic lesions at the H19 locus in Wilm's tumour patients", *Nature Genetics,* vol. 7, pp. 440–447, (1994).

Nagai, Hisaki, et al., "Cloning of No t I–Cleaved Genomic DNA Fragments Appearing as Spots in 2D Gel Electrophoresis", *Biochem. Biophys. Res. Commun.,* vol. 213, pp. 258–265, (1995).

Naidoo, Chetty R., et al., "Allelic Imbalance and Microsatellite Instability of the DCC Gene in Colorectal Cancer in Patients under the Age of 35 using Fluorescent DNA Technology", *Journal of Clinical Pathology,* vol. 51(1), pp. 35–38, (1998), abstract only.

Naumova, A., et al., "Concordance between Parental Origin of Chromosome 13q Loss and Chromosome 6p Duplication in Sporadic Retinoblastoma", Am. J. Hum. Genet., vol. 54, pp. 274–281, (1994).

Newman, Beth, et al., "Frequency of Breast Cancer Attributable to BRCA1 in a Population–Based Series of American Women", JAMA, vol. 279, pp. 915–921, (1998).

Nicholls, Robert D., et al., "Genetic imprinting suggested by maternal heterodisomy in non–deletion Prader Willi syndrome", Nature, vol. 342, pp. 281–285, (1989).

Nicholls, Robert D., "Genomic imprinting and candidtate genes in the Prader–Willi and Angelman syndromes", *Genetics and Development,* vol. 3, No. 3, (1993).

Nowell, P.C. "The Clonal Evolution of Tumor Cell Population", *Science,* vol. 194, pp. 23–28, (1976).

Ogawa, O., et al., "Constitutional relaxation of insulin–like growth factor II gene imprinting associated with Wilm's tumour and gigantism", Nat. Genet., vol. 5, pp. 408–412, (1993).

Ogawa, O., et al., "Relaxation of insulin–like growth factor II gene imprinting implicated in Wilm's tumour", *Nature,* vol. 362, (Apr. 1993).

Ohlsson, Rolf, et al., "IGF2 is parentally imprinted during human embryogenesis and in the Beckwith–Wiedemann syndrome", Nature Genetics, vol. 4, pp. 94–97, (1993).

Ottini, Laura, et al., "Mi rosatellite Instability in Gastric Cancer is Associated with Tumor Location and Family History in a High–Risk Population from Tuscany", *Cancer Research,* vol. 57, pp. 4523–4529, (1997).

Piao, Kim H., et al., "Expression of HMSH2 and HMLH1 in Colorectal Carcinomas with Microsatellite Instability", *Pathology, Research & Practice,* vol. 194 (1), pp. 3–9, (1998), (Abstract only).

Ping, April Joy, et al., "Genetic Linkage of Beckwith–Wiedemann Syndrome to 11p15", *Am. J. Hum. Genet.,* vol. 44, pp. 720–723, (1989).

Reeve, Anthony E., et al., "Loss of Allelic Heterozygosity at a Second Locus on Chromosome 11 in Sporadic Wilms' Tumor Cells", *Molecular and Cellular Biology,* vol. 9, pp. 1799–1803, (1989).

Reik, W., et al., "Allelic methylation of H19 and IGF2 in the Beckwith–Wiedemann syndrome", Cell, vol. 81, pp. 197–205, (1995).

Reik, Wolf, et al., "Imprinting mutations in the Beckwith–Wiedemann syndrome suggested by an altered imprinting pattern in the IGF2–H19 domain", Human Molecular Genetics, vol. 4, pp. 2379–2385, (1995).

Rainier, Shirley, et al., "Capture and characterization of 5–aza–2'–deoxycytidine–treated C3H/10T/1/2cells prior to transformation", Proc. Natl. Acad. Sci. USA, vol. 85, pp. 6384–6388, (1988).

Rainier, Shirley, et al., "Loss of Imprinting in Hepatoblastoma", Cancer Research, vol. 55, pp. 1836–1838, (1995).

Rainier, Shirley, et al., "Relaxation of imprinted genes in human cancer", Nature, vol. 362, pp. 747–749, (1993).

Randhawa, Gurvaneet S., et al., "Loss of Imprinting in Disease Progression in Chronic Myelogenous Leukemia", Blood, vol. 91, pp. 3144–3147, (1998).

Roberts, S.G.E., et al., "Activator–induced conformational change in general transcription factor TFIIB", Nature, vol. 371, pp. 717–714, (1994).

Sapienza, Carmen, et al., "Epigenetic and genetic factors affect transgene methylation imprinting", Development, vol. 107, pp. 165–168, (1989).

Schroeder, Wanda T., et al., "Nonrandom Loss of Maternal Chromosome 11 Alleles in Wilms Tumors", Am. J. Hum. Genet., vol. 40, pp. 413–420, (1987).

Schawrtz, Peter J., et al., "Prolongation of the QT Interval and the Sudden Infant Death Syndrome", The New England Journal of Medicine, vol. 338, pp. 1709–1714, (1998).

Scrable, Heidi, et al., "A model for embryonal rhabdomyosarcoma tumorigenesis that involves genome imprinting", Proc. Natl. Acad. Sci. USA, vol. 86, pp. 7480–7484, (1989).

Sekine, Ikuo, et al., "Microsatellite Instability in Lung Cancer Patients 40 Years of Age or Younger", Jpn. J. Cancer Res., vol. 88, pp. 559–563, (1997).

Senba, Shingo, et al., "Clinicopatholgic and Genetic Features of Nonfamilial Colorectal Carcinomas with DNA Replication Errors", Cancer, vol. 82, pp. 279–285, (1998).

Shinmura, Kazuya, et al., "Stage–dependent Evaluation of Microsatellite Instability in Gastric Carcinoma with Familial Clustering", Cancer Epidemiology, Biomarkers & Prevention, vol. 6, pp. 693–697, (1997).

Steenman, Marja J., et al., "Loss of imprinting of IGF2 is linked to reduced expression and abnormal methylation of H19 in Wilms' tumour", Nature Genetics, vol. 7, pp. 433–439, (1994).

Stoger, R., et al., "Maternal–Specific Methylation of the Imprinted Mouse Igf2r Locus Identifies the Expressed Locus as Carrying the Imprinting Signal", Cell, vol. 73, pp. 61–71, (1993).

Strahl–Bolsinger, Sabine, et al., "SIR2 and SIR4 interactions differ in core and extended telomeric heterochromatin in yeast", Genes & Development, vol. 11, pp. 82–93, (1997).

Suzuki, Hiroko, et al., "Altered imprinting in lung cancer", Nature Genetics, vol. 6, pp. 332–333, (1994).

Suzuki, K., et al., "Microsatellite instability in female non––small–cell lung cancer patients with familial clustering of malignancy", British Journal of Cancer, vol. 77(6), pp. 1003–1008, (1998).

Swain, Judith L., et al., "Parental Legacy Determines Methylation and Expression of an Autosomal Transgene: A Molecular Mechanism for Parental Imprinting", Cell, vol. 50, pp. 719–727, (1987).

Tartof, Kenneth D., et al., "Trans–Sensing Effects from Drosophila to Humans", Cell, vol. 65, pp. 201–203, (1991).

Taunton, Jack, et al., "A Mammalian Histone Deacetylase Related to the Yeast Transcriptional Regulator Rpd3p", Science, vol. 272, pp. 408–411, (1996).

Thibodeau, Stephen N., et al., "Microsatellite Instability in Colorectal Cancer: Different Mutator Phenotypes at the Principal Involvement of hMLH1", Cancer Research, vol. 58, pp. 1713–1718, (1998).

Thompson, Jeffrey S., et al., "Histone H3 amino terminus is required for telomeric and silent mating locus repression in yeast", Nature, vol. 369, pp. 245–247, (1994).

Thompson, Jeffrey S., et al., "Reduced Expression of the Cyclin–dependent Kinase Inhibitor Gene $p57^{KIP2}$ in Wilms' Tumor", Cancer Research, vol. 56, pp. 5533–5785, (1996).

Van der May, Andel G. L., et al., "Genomic Imprinting in Hereditary Glomus Tumours: Evidence for New Genetic Theory", The Lancet, vol. 11, pp. 1291–1294, (1989).

van Gurp, Ruud J. H. L. M., et al., "Biallelic Expression of the H19 and IGF2 Genes in Human Testicular Germ Cell Tumors", Journal of the National Cancer Institute, vol. 86, pp. 1070–1075, (1994).

Viljoen D., et al., "Evidence for paternal imprinting in familial Beckwith–Wiedemann syndrome", J. Med. Genet., vol. 29, pp. 221–225, (1992).

Vogelsang, H. E., et al., "Microsatellite instability and positive family anamnesis in patients with stomach carcinoma", Langerbecks Archiv fur Chirurgie–Supplement–Kongressband, vol. 114, pp. 113–116, (1997), (German), untranslated, (abstract only).

Vu, Thanh H., et al., "Insulin–Like Growth Factor II in Uterine Smooth–Muscle Tumors: Maintenance of Genomic Imprinting in Leiomyomata and Loss of Imprinting in Leiomyosarcomata", Journal of Clinical Endocrinology and Metabolism, vol. 80, pp. 1670–1676, (1995).

Walters, Mark C., et al., "Transcriptional enhancers act in cis to suppress position–effect variegation", Genes & Development, vol. 10, pp. 185–195, (1996).

Weksberg, Rosanna, et al., "Disruption of insulin–like growth factor 2 imprinting in Beckwith–Wiedemann Syndrome", Nature Genetics, vol. 5, pp. 143–150, (1993).

White, Lisa M., et al., "Allele–Specific Replication of 15q11–q13 Loci: A Diagnostic Test for Detection of Uniparental Disomy", Am. J. Hum. Genet., vol. 59, pp. 423–430, (1996).

Wolffe, A. P., "Inheritance of chromatin states", Dev. Genet., vol. 15, pp. 463–470, (1994).

Zhan, Shili, et al., "Loss of imprinting of IGF2 in Ewing's sarcoma", Oncogene, vol. 11, pp. 2503–2507, (1995).

Zhan, Shli, et al., "Activation of an Imprinted Allele of the Insulin–like Growth Factor II Gene Implicated in Rhabdosarcoma", Journal of Clinical Investigation, vol. 94, pp. 445–448.

Zhang, Yonghui, et al, "Monoallelic expression of the human H19 gene", Nature Genetics, vol. 1, pp. 40–44, (1992).

* cited by examiner

FIGURE 2A

METHODS AND KITS FOR DIAGNOSING AND DETERMINATION OF THE PREDISPOSITION FOR DISEASES

This application is a continuation-in-part of application Ser. No. 08/995,150 filed Dec. 29, 1997, now abandoned and which claims priority to International Application No. PCT/US97/23991 filed Dec. 29, 1997, now in national phase in Europe, Australia, Japan and Canada, both of which claim priority to U.S. Provisional Patent Application Ser. No. 60/034,095, filed Dec. 30, 1996 now abandoned.

This invention was made with Government support under grants from the National Institutes of Health. The United States Government may have certain rights in the claimed invention.

FIELD OF THE INVENTION

The present invention relates to methods for detecting and/or screening for the presence of diseases such as cancer, and for assessing the risk of contracting a disease. The present invention also relates to methods for detecting and/or screening for the presence of DNA microsatellite instability.

BACKGROUND OF THE INVENTION

The single greatest impediment to cancer diagnosis is the general requirement that the tumor itself must be detected directly. Efforts to identify genetic abnormalities in normal tissues of patients with cancer or at risk of cancer have been disappointing. For example, BRCA1 mutations are present in only about 1% of breast cancers. A small fraction of patients with colorectal cancer have predisposing mutations in the APC gene (>1%), causing adenomatous polyposis coli. An even smaller fraction show mutations in genes responsible for replication error repair (>2% of colon cancer patients, or much less than 1% of the population), show mutations in genes responsible for nucleotide mismatch error repair causing hereditary nonpolyposis colorectal cancer (HNPCC or Lynch syndrome).

Genetic studies of colorectal cancer present a paradox, in that 15–40% of sporadically occurring tumors show DNA microsatellite instability, depending on the number of microsatellite markers that are used to detect it, even though the overwhelming majority of such tumors do not show mutations in known error repair genes. Furthermore, microsatellite instability in many common tumors, including those of the stomach, colon, and lung, is associated with a younger age, positive family history, and/or less accessible and detectable location, suggesting that a relatively large subgroup of cancer patients in the general population are at increased risk of cancer, even though they do not fall within a well-defined syndrome.

Microsatellite instability, in particular, requires for identification that a patient already have a tumor, because the assay compares microsatellite marker length between the monoclonal tumor cell population and normal tissue derived from the same patient. Most importantly, family history still remains the most reliable diagnostic procedure for identifying patients at risk of cancer. A molecular diagnostic approach that might identify patients with cancer or at risk of cancer, using only normal tissue, would offer a decisive advantage for intervention and treatment.

Thus, there remains a need for a diagnostic method for detecting and/or screening for the presence of diseases and/or the risk of contracting a disease. In particular, there remains a need for a method for detecting and/or screening for the presence of cancer, which does not require a tumor sample. There also remains a need for a method of detecting and/or screening for the presence of cancer and/or the risk of contracting cancer which can be applied to a wide section of the population. There also remains a need for a method of detecting and/or screening for the presence of replication error repair defects which does not require a tumor sample. There also remains a need for a method for quantifying the degree of loss of imprinting. There also remains a need for a method for screening infants for the risk of sudden infant death syndrome (SIDS). There also remains a need for kits for carrying out these methods.

SUMMARY OF THE INVENTION

The present invention provides a method and a kit for the purpose of diagnosing a disease by measuring abnormalities in imprinting of a gene or population of genes. The disease that can be diagnosed by the present invention is selected from any disease that is mediated by, or is associated with, a particular gene or combination of genes that are subject to imprinting. According the present invention, the imprinting can be abnormally on or can be abnormally off or partially abnormally on or off. In those cases where the particular gene that is being examined is normally imprinted, but in the disease state is abnormally not imprinted, the present invention is designed to detect the "loss of imprinting" (hereinafter "LOI") thereby indicating that the disease may be present.

The diseases that can be diagnosed according to the present invention includes, but is not limited to, cancers, SIDS, birth defects, mental retardation, diabetes & gestational diabetes. Cancers that can be diagnosed according to the present invention include, but are not limited to, colorectal cancer, esophageal cancer, stomach cancer, leukemia/lymphoma, lung cancer, prostate cancer, uterine cancer, breast cancer, skin cancer, endocrine cancer, urinary cancer, pancreatic cancer, other gastrointestinal cancer, ovarian cancer, cervical cancer, head cancer, neck cancer, and adenomas.

The present invention also provides a method and a kit for determining if a patient is predispositioned to a particular disease. In this case, normal tissue can be tested to determine whether there is abnormal imprinting for a particular gene or combination of genes. If the imprinting is abnormal, e.g., either abnormally on or abnormally off, then the patient may have a predisposition for a particular disease. Appropriate screening of other factors can then be done a periodic intervals to be able to detect the disease early.

Because the present invention is particularly useful for determining if a patient is predispositioned for a particular disease, such as cancer, the present invention is particularly useful for screening populations of individuals to determine if individuals are predispositioned for a particular disease. By having the capability of efficiently screening a large population of individuals for a particular disease, e.g., colon cancer, individuals that have the cancer in the early stages or individuals that are predispositioned for the cancer can be identified early and appropriate treatment can be initiated.

According to the present invention, the testing of an individual to determine if imprinting of a gene is normal or abnormal can be done on a wide variety of tissues. For example, in a test for colorectal cancer, one does not have to test tissue from the colon, but can test tissue from other parts of the body, including, but not limited to, blood cells, skin, hair, etc. Therefore, the present invention provides a method of testing any tissue in the body for a disease that is specific for a particular tissue in the body.

Analysis of imprinting of genes of biological tissues and cells to be used for transplantation can be performed according to the present invention to avoid the possibility of increasing a disease risk in the transplant recipient. Examples of tissues or cells that can be analyzed according to the present invention includes, but is not limited to, skin grafts, ligaments, eyes, kidney, liver, heart valves, lung, bone-marrow (Leukemia), neural tissue-embryonic neural tissue (used for variety of purposes such as increase dopamine production in Parkinson's patients, increase acetylcholine production in Alzheimer's patients, for enhancement of plasticity (norepinephrine), increase production of hypothalamic hypophysiotropic factors, development of neocortical cells, motor neurons, sensory neurons, blood-white cells and others of myelocyte lineage, muscle-myoblasts, seeding of "blast cells," and genetically engineered cells for administration to patients.

According to one embodiment of the present invention, there is a strong correlation between the presence or absence of LOI in a subject's somatic cells and the presence of disease and/or the risk of contracting a disease. There is a strong correlation between the presence of LOI in a subject's somatic cells and the presence of replication repair error defects. There is also a strong correlation between the degree of LOI present in a subject's somatic cells and the presence of cancer and/or the risk of contracting cancer. In addition, there is a strong correlation between the degree of LOI present in a subject's somatic cells and the degree of replication repair error defects present in a subject's somatic cells. There is a strong correlation between the degree of LOI present in a subject's somatic cells and the survival rate of the subject upon contracting cancer. According to the present invention, the general population, in particular infants, may be screened for the risk of genetic diseases, in particular SIDS, by examining their imprinting patterns.

Accordingly, it is an object of the present invention to provide novel methods for detecting or determining a predisposition for the presence of a disease in an individual.

It is another object of the present invention to provide novel methods for detecting and/or screening for the presence of colorectal cancer.

It is yet another object of the present invention to provide novel methods for detecting and/or screening for the presence of stomach cancer.

It is another object of the present invention to provide novel methods for detecting and/or screening for the presence of esophageal cancer.

It is another object of the present invention to provide novel methods for detecting and/or screening for the presence of leukemia.

It is another object of the present invention to provide novel methods for detecting and/or screening for the presence of lung cancer.

It is yet another object of the present invention to provide novel methods for detecting and/or screening for the presence of prostate cancer.

It is another object of the present invention to provide novel methods for detecting and/or screening for the presence of uterine cancer.

It is another object of the present invention to provide novel methods for detecting and/or screening for the presence of breast cancer.

It is another object of the present invention to provide novel methods for detecting and/or screening for the presence of skin cancer.

It is another object of the present invention to provide novel methods for detecting and/or screening for the presence of endocrine cancer.

It is another object of the present invention to provide novel methods for detecting and/or screening for the presence of urinary cancer.

It is another object of the present invention to provide novel methods for detecting and/or screening for the presence of lymphoma.

It is another object of the present invention to provide novel methods for detecting and/or screening for the presence of pancreas cancer.

It is another object of the present invention to provide novel methods for detecting and/or screening for the presence of gastrointestinal cancer.

It is another object of the present invention to provide novel methods for detecting and/or screening for the presence of ovarian cancer.

It is another object of the present invention to provide novel methods for detecting and/or screening for the presence of cervical cancer.

It is another object of the present invention to provide novel methods for detecting and/or screening for the presence of head cancer.

It is another object of the present invention to provide novel methods for detecting and/or screening for the presence of neck cancer.

It is another object of the present invention to provide novel methods for detecting and/or screening for the presence of adenomas.

It is another object of the present invention to provide novel methods for detecting and/or screening for the presence of replication error repair defects.

It is another object of the present invention to provide novel methods for assessing the risk of contracting cancer.

It is another object of the present invention to provide novel methods for assessing the risk of contracting colorectal cancer.

It is another object of the present invention to provide novel methods for assessing the risk of contracting stomach cancer.

It is another object of the present invention to provide novel methods for assessing the risk of contracting esophageal cancer.

It is another object of the present invention to provide novel methods for assessing the risk of contracting leukemia.

It is another object of the present invention to provide novel methods for assessing the risk of lung cancer. It is another object of the present invention to provide novel methods for assessing the risk of contracting prostate cancer.

It is another object of the present invention to provide novel methods for assessing the risk of contracting uterine cancer.

It is another object of the present invention to provide novel methods for assessing the risk of contracting breast cancer.

It is another object of the present invention to provide novel methods for assessing the risk of contracting skin cancer.

It is another object of the present invention to provide novel methods for assessing the risk of contracting endocrine cancer.

It is another object of the present invention to provide novel methods for assessing the risk of contracting urinary cancer.

It is another object of the present invention to provide novel methods for assessing the risk of contracting lymphoma.

It is another object of the present invention to provide novel methods for assessing the risk of contracting pancreas cancer.

It is another object of the present invention to provide novel methods for assessing the risk of contracting gastrointestinal cancer.

It is another object of the present invention to provide novel methods for assessing the risk of contracting ovarian cancer.

It is another object of the present invention to provide novel methods for assessing the risk of contracting cervical cancer.

It is another object of the present invention to provide novel methods for assessing the risk of contracting head cancer.

It is another object of the present invention to provide novel methods for assessing the risk of contracting neck cancer.

It is another object of the present invention to provide novel methods for assessing the risk of contracting adenomas.

It is another object of the present invention to provide novel methods for identifying a subset of the general population for preventative chemotherapy.

It is another object of the present invention to provide novel methods for identifying a subset of the general population for cancer treatment.

It is another object of the present invention to provide novel methods for quantifying the degree LOI.

It is another object of the present invention to provide novel methods for determining the prognosis of a patient suffering from cancer.

It is another object of the present invention to provide novel methods for determining the future prognosis, upon contracting cancer, of a subject who does not yet have cancer.

It is another object of the present invention to provide novel methods for screening the general population, in particular infants, for genetic diseases.

It is another object of the present invention to provide novel methods for screening infants for the risk of SIDS.

It is another object of the present invention to provide novel kits useful for carrying out such methods.

These and other objects, features and advantages of the present invention will become apparent after a review of the following detailed description of the disclosed embodiments.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIGS. 2A and 2B show genomic imprinting in colorectal cancer and non-cancer patients; FIG. 2A LOI is seen in both cancer (C) and matched normal (N) mucosa from patients 1, 2, and 4, who also showed microsatellite instability in their cancers. Normal imprinting is seen in both cancer (C) and paired normal (N) mucosa from patients 19 and 21, who did not show microsatellite instability in their cancers. The A and B alleles are 292 and 229 bp, respectively. FIG. 2B normal imprinting is seen in the normal mucosa of noncancer patients 1–7. Slight expression of the A allele is seen in patient 3, at a 1:5.2 ratio to the B allele, below the threshold for scoring LOI.

DETAILED DESCRIPTION

Figure 1:
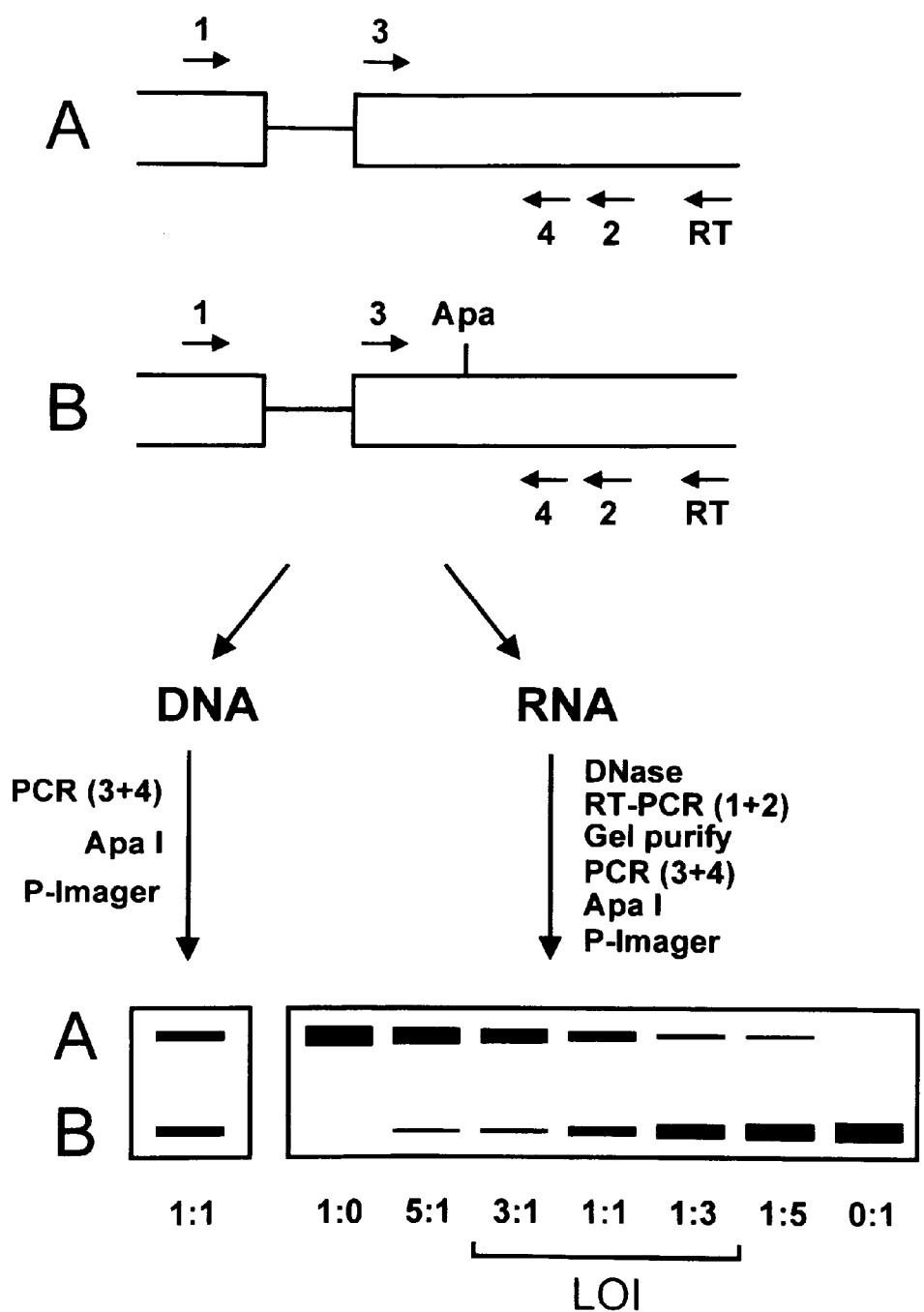
FIG. 1 schematically shows the strategy for quantitative analysis of IGF2 imprinting in colon cancer. One of the two polymorphisms used, an Apa I site in exon 9, is depicted for illustrating the method. A heterozygous (informative) sample harbors two alleles, A (without the Apa I site), and B (with the Apa I site). Heterozygosity of genomic DNA was ascertained by performing DNA PCR, using primers 3 and 4 across the Apa I site, and the PCR product was digested with Apa I. Imprinting status was ascertained by performing RT-PCR on RNA, using primers 1 and 2 in exons 8 and 9, respectively. The cDNA PCR product, which is shorter than any possible contaminating genomic DNA product because of intron splicing, was electrophoresed and purified from an agarose gel. PCR was then performed using primers 3 and 4, end-labeling one of the primers. The PCR product was digested with Apa I, analyzed on a 6% polyacrylamide gel, and quantified on a PhosphorImager. The B allele is shorter but of equal radioactive intensity to the A allele. All RT-PCR experiments were performed in parallel in the presence and absence of reverse transcriptase, from the identical cDNA product, in order to rule out the presence of contaminating DNA. The threshold for scoring loss of imprinting (LOI) was less than a 3:1 ratio between the more abundant and less abundant alleles. This threshold distinguished both cancers and matched normal mucosa with microsatellite instability in their tumors. The quantitative measure of imprinting was reproducible among assays, and also consistent between paired tumor and normal samples by paired t-test analysis.

The present invention provides a novel method for detecting a disease or measuring the predisposition of a subject for developing a disease in the future by obtaining a biological sample from a subject; and screening the biological sample for the presence of abnormal imprinting. In the present invention, the subject will typically be a human but also is any organism, including, but not limited to, a dog, cat, rabbit, cow, bird, ratite, horse, pig, monkey, etc.

If the disease to be detected is cancer, the cancer to be detected or screened includes, but is not limited to, colorectal cancer, esophageal cancer, stomach cancer, leukemia/lymphoma, lung cancer, prostate cancer, uterine cancer, breast cancer, skin cancer, endocrine cancer, urinary cancer, pancreas cancer, other gastrointestinal cancer, ovarian cancer, cervical cancer, head cancer, neck cancer, and adenomas. In a particularly preferred embodiment, the cancer is colorectal cancer.

The biological sample may be any which is conveniently taken from the patient and contains sufficient information to yield reliable results. Typically, the biological sample will be a tissue sample which contains 1 to 10,000,000, preferably 1000 to 10,000,000, more preferably 1,000,000 to 10,000,000 somatic cells. However, it is possible to obtain samples which contain smaller numbers of cells and then enrich the cells. In addition, with certain highly sensitive assays (e.g., RT-PCR when IGF2 is abundant, and other methods like DNA methylation even when IGF2 not abundant) it is possible to get sample size down to single cell level-with. However, the sample need not contain any intact cells, so long as it contains sufficient biological material (e.g., protein; genetic material, such as DNA or RNA; etc.) to assess the presence or absence of LOI in the subject.

According to the present invention, the biological or tissue sample may be preferably drawn from the tissue which is susceptible to the type of disease to which the detection test is directed. For example, the tissue may be obtained by surgery, biopsy, swab, stool, or other collection method. In addition, it is possible to use a blood sample and screen either the mononuclear cells present in the blood or first enrich the small amount of circulating cells from the tissue of interest, i.e., colon, breast, etc. using a method known in the art.

According to one embodiment of the present invention, when examining a biological sample to detect colorectal cancer, it may be preferred to obtain a tissue sample from the colon. Such a tissue sample may be obtained by any of the above described methods, but the use of a swab or biopsy may be preferred. In the case of stomach and esophageal cancers, the tissue sample may be obtained by endoscopic biopsy or aspiration, or stool sample or saliva sample. In the case of leukemia, the tissue sample is preferably a blood sample.

In another preferred embodiment of the present invention, the biological sample is a blood sample. The blood sample may be obtained in any conventional way, such as finger prick or phlebotomy. Suitably, the blood sample is approximately 0.1 to 20 ml, preferably approximately 1 to 15 ml with the preferred volume of blood being approximately 10 ml.

In one preferred embodiment, the cancer to be detected is colorectal cancer, and the biological sample is a tissue sample obtained from the colon or a stool sample. In another preferred embodiment, the cancer to be detected is stomach cancer or esophageal cancer, and the tissue may be obtained by endoscopic biopsy or aspiration, or stool sample or saliva sample. In another preferred embodiment, the cancer to be detected is esophageal cancer, and the tissue is obtained by endoscopic biopsy, aspiration, or oral or saliva sample. In another preferred embodiment, the cancer is leukemia/lymphoma and the tissue sample is blood.

Genomic imprinting is an epigenetic modification of a specific parental chromosome in the gamete or zygote that leads to monoallelic or differential expression of the two alleles of a gene in somatic cells of the offspring. Imprinting affects various essential cellular and developmental processes, including intercellular signaling, RNA processing, cell cycle control, and promotion or inhibition of cellular division and growth.

The first deduction of imprinting at the single gene level involved a transgenic C-myc gene which showed dependence of its expression on paternal inheritance. The silent maternally inherited copy was methylated (Swain et al. (1987) *Cell* 50:719–727). Disruption of the insulin-like growth factor II (IGF2) gene in knockout experiments showed that IGF2 is imprinted and expressed normally only from the paternal allele, and that IGF2 is biparentally expressed in two neural tissues, the choroid plexus and the leptomeninges (DeChiara et al. (1991) *Cell* 64:849–859). These milestone studies showed that genomic imprinting affects normal endogenous genes and that imprinting shows tissue-specific regulation.

Direct approaches for the identification of novel imprinted genes include: positional cloning which identifies imprinted genes near other known imprinted genes (Barlow et al. (1991) *Nature* 349:84–87); comparing gene expression in parthenogenetic embryos to that of normal embryos (Kuroiwa et al. (1996) *Nat. Genet* 12:186–190); and restriction landmark genome scanning (Nagai et al. (1995) *Biochem. Biophys. Res. Commun.* 213:258–265).

Abnormalities of a single gene can affect imprinting of a proximate genomic region and disrupt multiple disease-causing genes, the phenotype depending upon the parental origin of the mutated gene. Two examples of imprinted human disease loci in close proximity are on chromosome 15. Disrupted imprinting of these loci is one of the causes of Prader-Willi syndrome (PWS) and Angelman sypdrome (AS) which involve mental retardation. PWS also causes obesity, and AS involves gross motor disturbances. Each disorder can be caused by parental-origin specific uniparental disomy (UPD) (Nicholls et al. (1989) *Nature* 342:281–285; Knoll et al. (1990) *Am. J. Hum. Genet.* 47: 149–155) or chromosomal deletions (Knoll et al. (1989) *Am. L Hum. Genet.* 47:149–155; Mattel et al. (1984) *Hum. Genet.* 66:313–334). The AS gene has not been isolated to date. PWS appears to be due to mutations or deletions in the small nuclear ribonucleoprotein polypeptide N (SNRPN) gene (reviewed in Nicholls et al. (1993) *Curr. Opin. Genet. Dev.* 3:445–446). A mutation affecting splicing of an untranslated upstream exon of SNRPN can also lead to AS, as well as abnormal imprinting of other loci (Dittrich et al. (1996) *Nat. Genet.* 14: 163–170).

It is likely that many more additional imprinted human disease loci will he identified, because UPD for specific chromosomes is often associated with multiple congenital anomalies (Ledbetter, D. H. and Engel, E. (1995) *Hum. Mol. Genet.* 4:1757–1764). Chromosomes that likely show this phenomenon include 2, 6, 7, 11, 14, 15, 16, 20, and X (Ledbetter, D. H. and Engel, E. (1995) *Hum. Mol. Genet.* 4:1757–1764).

An indirect suggestion of genomic imprinting in cancer came from investigations of the two embryonic tumors, hydatidiform mole and complete ovarian teratoma, showing that not only 46 chromosomes are required to create a normal embryo, but also a balance of maternal and paternal chromosomes. A relative imbalance leads to neoplastic growth, and the type of neoplasm depends upon whether there is a maternal or paternal genetic excess.

Another tumor apparently associated with imprinting is familial paraganglioma or glomus tumor. In all cases, the transmitting parent is the father (Van der Mey et al. (1989) Lancet 2:1291–1294). The gene has recently been localized to 11q22.3–q23 (Heutink et al. (1994) Eur. J. Hum. Genet 2:148–158).

Loss of heterozygosity (LOH) in the childhood Wilms tumor occurs on chromosome 11 and the specifically involved region is 11p15 (Reeve et al. (1989) Mol. Cell. Biol. 9:1799–1803). Schroeder et al. (1987) Am. J. Hum. Genet. 40:413–420, noted that in five of five cases of LOH, it was the maternal allele that was lost. This observation has been extended to other tumors of embryonic origin such as hepatoblastoma and rhabdomyosarcoma (Scrable et al. (1989) Proc. Natl. Acad. Sci. USA 86:7480–7484).

The N-myc gene on chromosome 2 shows preferential amplification of the paternal allele in neuroblastoma (Cheng et al. (1993) Nature Genet. 4:187–190). Advanced neuroblastoma tumors, showing N-myc amplification, also show preferential LOH of maternal chromosome 1, whereas earlier stage tumors without N-myc amplification do not (Caron et al. (1995) Hum. Mol. Genet 4:535–539). Thus, genetic disturbances involving imprinted genes in a given type of cancer may involve multiple chromosomes concurrently. Naumova et al. (1994) Am. J. Hum. Genet. 54:274–281, found transmission ratio distortion, concordance of 13q loss and isochromosome 6 of the same parental origin in retinoblastoma, again consistent with a mechanism of generalized disturbance of imprinting in embryogenesis leading to increased cancer risk.

Beckwith-Wiedemann syndrome (BWS) is a disorder of prenatal overgrowth and cancer, transmitted as an autosomal dominant trait, or arising sporadically. A clue to a role for genomic imprinting is increased disease penetrance when BWS is inherited from the mother (Viljoen, D. and Ramesar, R. (1992)]. Med. Genet. 29:22 1–225). The tumors of children show preferential loss of maternal 11p15 (Schroeder et al. (1987) Am. J. Hum. Genet. 40:413–420; Scrable et al. (1989) Proc. Natl. Acad. Sci. USA 86:7480–7484), suggesting that an imprinted locus could cause BWS and also be involved in sporadically occurring tumors. Genetic linkage analysis showed that BWS localizes to 11p13, consistent with this idea of generalized disruption, and not to 11p13, to which the WT1 gene had been localized (Ping et al. (1989) Am. J. Hum. Genet. 44:720–723; Koufos et al. (1989) Am. J. Hum. Genet. 44:711–719).

More direct evidence for genomic imprinting of 11p15 in BWS came from studies showing that some patients with BWS have paternal UPD, involving a region extending from the β-globin locus to the RAS gene (Henry et al. (1991) Nature 35:609–610). While the large 10 Mb region does not provide precise localization of an imprinted gene, it provides a foundation for later studies of imprinted loci on this chromosome.

Examination of RNA from Wilms tumor (WT) led to a discovery that not one but both IGF2 alleles were expressed in 70% of Wilms tumors (Rainier et al. (1993) Nature 362:747–749; Ohlsson et al. (1993) Nature Genet. 4:94–97). In addition, in 30% of cases, both alleles of H19 were expressed (Rainier et al. (1993) Nature 362:747–749). In contrast, examination of RNA from normal tissue shows normal imprinting with the expression of one allele of IGF2 and H19. This was the first evidence of imprinting in humans. The term for this novel genetic alteration is loss of imprinting (LOI) (Rainier et al. (1993) Nature 362:747–749) which simply means loss of preferential parental origin-specific gene expression and can involve either abnormal expression of the normally silent allele, leading to biallelic expression, or silencing of the normally expressed allele, leading to epigenetic silencing of the locus (Rainier et al. (1993) Nature 362:747–749; Feinberg (1993) Nature Genet. 4:110–113; Feinberg et al. (1995) J. Natl. Cancer Inst. Monographs 17:21–26). Thus, abnormal imprinting in cancer can lead to activation of normally silent alleles of growth-promoting genes (Rainier et al. (1993) Nature 362:747–749); (Feinberg (1993) Nature Genet. 4:110–113); (Feinberg et al. (1995) J Natl. Cancer Inst. Monographs 17:21–26).

Subsequently, LOI has been implicated in various tumor types. At first, LOI was found in other childhood tumors, such as hepatoblastoma (Rainier et al. (1995) Cancer Res. 55: 1836–1838; Li et al. (1995) Oncogene 11:221–229), rhabdomyosarcoma (Zhan et al. (1994) J Clin. Invest. 94:445–448), and Ewings sarcoma (Zhan et al. (1995a) Oncogene 11:2503–2507). LOI of IGF2 and H19 have also now been found in many adult tumors, including uterine (Vu et al. (1995) J. Clin. Endocrinol. Metab. 80:16701676 cervical (Doucrasy 12:423430), esophageal (Hibi et al. (1996) Cancer Res. et al. (1996) Onco gene 56480–482), prostate (Jartard et al. (1995) Clin. Cancer Res. 1:14711478), lung cancer (Kondo et al. (1995) Oncogene 10:1193–1198), choriocarcinoma (Hashimoto et al. (1995) Nat. Genet. 9:109–110), germ cell tumors (Van Gurp et al. (1994) J. Natl. Cancer Inst. 86:1070–1075) BWS (Steenman et al. (1994) Nature Genet. 7:433–437) Weksberg et al. (1993) Nature Genet. 5:143–150) and Wilms tumor (Ogawa et al. (1993) Nature Genet. 5:408–412). Thus, LOI is one of the most common alterations in human cancer.

Another imprinted gene in 11p5 is $p_{57}^{KIP2}$ a cyclin-dependent kinase (CDK) inhibitor similar in its CDK inhibitory domain to $p21^{WAF1/CiPi}$ a target of p53 (Matsuoka et cii. (1995) Genes Dev. 9:640–662); Lee et al. (1995) Genes Dev. 9:639–649). The gene was localized within 40 kb of a group of BWS balanced germline chromosomal rearrangement breakpoints, in contrast to IGF2 and H19, which are located telomeric to those breakpoints (Hoovers et al. (1995) Proc. Natl. Acad. Sci. USA 92: 12456–12460). Human $p_{57}^{KIP2}$ was found to be imprinted with preferential expression from the maternal allele (Matsuoka ci cii. (1996) Proc. Natl. Acad. Sci. USA 93:3026–3030). $p_{57}^{KIP2}$ also shows abnormal imprinting and epigenetic silencing in some tumors and BWS patients (Thompson et al. (1996) Cancer Research 56:5723–5727). Other imprinted genes on 11p15 include KvLQT1, TSSC3, TSSC5, and ASCL2. Abnormalities of one or more of these genes are implicated in a wide variety of cancers, and birth defects including BWS, SIDS (Schwartz P. J. et al., (1998) Prolongation of the QT Interval and the Sudden Infant Death Syndrome, New Engl. J. Med. 338:1709–1714).

Several lines of evidence provide a role for DNA methylation in the control of genomic imprinting. First, some imprinted genes in mice, such as H19, show parental origin-specific, tissue-independent methylation of CpG islands (Ferguson-Smith et al. (1993) Nature 362:751–755; Bartolomei et al. (1993) Genes Develop. 7:1663–1673). This methylation represents imprinting silencing on the paternal chromosome and is not secondary to changes in gene expression. Second, knockout mice deficient in DNA methyltransferase, and exhibiting widespread genomic hypomethylation, do not show allele-specific methylation of the H19 CpG island and exhibit biallelic expression of H19 and loss of expression of IGF2 (Li et al. (1993) *Nature* 366:362–365). Similar parental origin-specific methylation has also been observed for a CpG island in the first intron of the maternally inherited, expressed allele of the IGF2 receptor gene (IGF2R) (Stoger et al. (1993) *Cell* 73:61–71). Methyltransferase deficient knockout mice show loss of methylation of IGF2R and epigenetic silencing of the gene (Li et al. (1993) *Nature* 366:362–365).

Widespread alterations in DNA methylation in human tumors were discovered years ago (Feinberg, AP. (1983) *Nature Genet.* 4:110–113) and remain the most commonly found alteration in human cancers. These alterations are ubiquitous to both benign and malignant neoplasms (Goelz et al. (1985) *Science* 228:187–190). The precise role of these changes remain unclear; but, both decreased and increased methylation have been found at specific sites in tumors, with an overall decrease in quantitative DNA methylation (Feinberg et al. (1988) *Cancer Res.* 48:1159–1161; Feinberg, A. P. (1988) *Prog. Clin. Biol. Res.)* 79:309–317; Jones et al. (1990) *Adv. Cancer Res.* 54:1–23).

In humans, as in mice, the paternal allele of a CpG island in the H19 gene and its promoter is normally methylated, and the maternal allele is unmethylated (Steenman et al., (1994) *Nature Genet.* 7:433–439; Ferguson-Smith et al. (1993) *Nature* 362:751–755; Bartolomei et al. (1993) *Genes Develop.* 7:1663–1673). Because tumors with LOI of IGF2 showed reduced expression of H19, the methylation pattern of H19 has been examined in tumors with LOI. In all cases showing LOI of IGF2, the H19 promoter exhibits 90%-100% methylation at the sites normally unmethylated on the maternally inherited allele (Steenman et al. (1994) *Nature* 7:433–437; Moulton et al. (1994) *Nature Genet.* 7:440–447). Thus, the maternal allele has acquired a paternal pattern of methylation, consistent with observed expression of IGF2 on the same maternally derived chromosome in these tumors. In contrast, tumors without LOI of IGF2 show no change in the methylation of H19, indicating that these changes are related to abnormal imprinting and not malignancy per se (Steenman et at. (1994) *Nature Genet.* 7:433–439; Moulton et at. (1994) *Nature Genet.* 7:440–447). The same alterations in methylation of the maternal allele of H19 are found in BWS patients with LOI of IGF2 (Steenman et at. (1994) *Nature Genet.* 7:433–439; Reik et at. (1994) *Hum. Mat. Genet.* 3:1297–1301; Reik et at. (1995) *Hum. Mat. Genet.* 4:2379–2385).

A second potential mechanism of LOI may involve disruption of an imprinting control center on chromosome 11, similar to that recently described for the BWS/AS region of chromosome 15 (Dittrich et al. (1996) *Nat. Genet.* 14: 163–170). A cluster of five BWS balanced germline chromosomal rearrangement breakpoints lies between $p_{57}^{KIP2}$ on the centromeric side, and IGF2 and H19 on the telomeric side (Hoovers et al. (1995) *Proc. Natl. Acad. Sci. USA* 92:12456–12460). Thus, disruption of a gene spanning this region could cause abnormal imprinting, as well as BWS and/or cancer, at least when inherited through the germline.

Another potential mechanism for LOI involves loss of trans-acting factors which may establish and maintain a normal pattern of genomic imprinting once such a pattern is established in the germline. Trans-acting modifiers of imprinting are likely to exist, since imprinting of transgenes is host strain-dependent (Sapienza et al. (1990) *Develop.* 107:165–168; Allen et al. (1990) *Cell* 61:853–361). Such genes might thus act as tumor suppressor genes in humans and other species.

Yet another potential mechanism of imprinting that might be disrupted in cancer involves histone deacetylation which is linked to X-inactivation in mammals (reviewed in Wolffe, A. P. (1994) *Develop. Genet.* 15:463–470) and to telomere silencing in yeast (Thompson et al. (1994) *Nature* 369:245–247). Genes for both histone acetylase and histone deacetylase have recently been isolated (Brownell et al. (1996) *Cell* 84:843–851 Taunton et al. (1996) *Science* 272:408–411). In addition, telomere silencing in yeast also involves the action of specific genes, e.g., SIR1–SIR4, some of which have homologues in mammals (Brachmann et al. (1995) *Genes Develop.* 9:2888–2902). Similarly, some examples of gene silencing in mammals may resemble position-effect variation in Drosophila, a form of position-dependent epigenetic silencing (Walters et al. (1996) *Genes Develop.* 10:185–195). Finally, imprinted loci on maternal and paternal chromosomes may interact during DNA replication. Chromosomal regions harboring imprinted genes show replication and timing asynchrony (Kitsberg et al. (1993) *Nature* 364:459–463). Furthermore, the two parental homologues of some imprinted genes show nonrandom proximity in late S-phase (LaSalle. J. M. and Lalande, M. (1996) *Science* 272:725–728), suggesting some form of chromosomal cross-talk, as has been observed for epigenetic silencing in Drosophila (Tartoff, K. D. and Henikoff, S. (1991) *Cell* 65:201–203).

The human IGF2 and H19 genes are normally imprinted, i.e., show preferential expression of a specific parental allele (Rainier et al. (1993) *Nature* 362:747–749; Zhang, Y. and Tycko, B. (1992) *Nat. Genet.* 1:40–44; Giannoukakis et al. (1993) *Nat. Genet.* 4:98–101; Ohlsson et al. (1993) *Nature Genet.* 4:94–97; Ogawa et al. (1993b) *Nature* 362:749–751).

Furthermore, as discussed above, some tumors undergo loss of imprinting (LOI) in cancer, with one or more of the following:

biallelic expression of IGF2 (Rainier et al. (1993) *Nature* 362:747–749; Ogawa et al. (1993b) *Nature* 362:749–751), epigenetic silencing of H19 (Steenman et al. (1994) *Nature Genet.* 7:433–439; Moulton et al. (1994) *Nature Genet.* 7:440–447); and/or abnormal expression of the paternal H19 allele (Rainier et al. (1993) *Proc. Natl. Acad Sci. USA* 85:6384–6388), and this observation has been extended to a wide variety of childhood and adult malignancies (Rainier et al. (1993) *Proc. Natl. Acad. Sci. USA* 85:6384–6388; Suzuki et al. (1994) *Nat. Genet.* 6:332–333). Normal imprinting can be maintained in part by allele-specific, tissue-independent methylation of H19, since LOI is associated with abnormal methylation of the normally unmethylated maternal H19 allele (Steenman et al. (1994) *Nature Genet.* 7:433–439; Moulton et al. (1994) *Nature Genet.* 7:440–447). There are other imprint-specific marks of methylation that show alterations with LOI of 11p15 genes, including KvLQT1 and others.

However, the previous studies did not report any comparison of the rate of occurrence of LOI in the tumors or the matched normal tissue of a cancerous population to the rate of occurrence of LOI in the same tissue of a non-cancerous population. Thus, any findings of LOI in the matched normal tissue of the cancerous population have been previously explained in terms of tissue-specific normal LOI. Such explanations are consistent with the clonal theory of cancer, which attributes tumor generation to a spontaneous mutation leading uncontrolled growth of a particular clone (Norell, EC The Clonal Evolution of Tumor Cell Population, 1976

*Science* 149:23–28) and teaches against being able to detect a genetic marker of a predisposition to contracting cancer in normal cells. Biallelic expression of IGF2 in colorectal cancer has also been ascribed to a change in promoter usage rather than LOI (Issa et al. (1996) *Proc. Natl. Acad. Sci. USA* 93:11757–11762).

Moreover, the degree of LOI thus-far reported remains unquantified and unquantifiable. There is no indication that there is any relationship between the degree of LOI and the presence of cancer or the likelihood of developing cancer.

Furthermore, the previous studies have only sought to detect LOI in normal cells of the same tissue in which cancer is present. There is no indication that there is any relationship between the presence, absence, or degree of LOI in one tissue and the presence or likelihood of developing cancer in a different tissue.

It would also be desirable to be able to make some prediction or assessment about the chances of survival once a patient has contracted cancer. It would be especially beneficial if such predictions could be made before the patient actually contracted cancer. With such a prediction in hand, it would be possible to make better decisions about the examination of the patient prior to the detection of cancer, as well as the treatment of the patient after the detection of cancer.

Sudden infant death syndrome (SIDS) remains a significant killer. It would be useful if infants could be screened for any predisposition to SIDS, so preventative steps could be taken. SIDS has recently been shown to be caused by heart arrhythmias caused by prolongation of the long QT interval, which is controlled in part by the KvLQT1 gene, which is normally imprinted. The imprinting of KvLQT1 is disturbed in varying degrees in the infant population. However, to date there is no method effective for screening infants for the risk of SIDS.

The presence or absence of LOI may be detected by examining any condition, state, or phenomenon which causes LOI or is the result of LOI. Such conditions, states, and phenomena include, but are not limited to 1. Causes of LOI, such as the state or condition of the cellular machinery for DNA methylation, the state of the imprinting control region on chromosome 11, the presence of trans-acting modifiers of imprinting, the degree or presence of histone deacetylation;
2. State of the genomic DNA associated with the genes or gene for which LOI is being assessed, such as the degree of DNA methylation;
3. Effects of LOI, such as:
    a. Relative transcription of the two alleles of the genes or gene for which LOI is being assessed;
    b. Post-transcriptional effects associated with the differential expression of the two alleles of the genes or gene for which LOI is being assessed;
    c. Relative translational of the two alleles of the genes or gene for which LOI is being assessed;
    d. Post-translational effects associated with the differential expression of the two alleles of the genes or gene for which LOI is being assessed;
    e. Other downstream effects of LOI, such as altered gene expression measured at the RNA level, at the splicing level, or at the protein level or post-translational level (i.e., measure one or more of these properties of an imprinted gene's manifestation into various macromolecules); changes in function that could involve, for example, cell cycle, signal transduction, ion channels, membrane potential, cell division, or others (i.e., measure the biological consequences of a specific imprinted gene being normally or not normally imprinted (for example, QT interval of the heart). Another group of macromolecular changes could be in associated processes such as histone acetylation, histone deacetylation, or RNA splicing.

When detecting the presence or absence of LOI by relying on any one of these conditions, states, or phenomena, it is possible to use a number of different specific analytical techniques. In particular, it is possible to use any of the methods for determining the pattern of imprinting known in the art. It is recognized that the methods may vary depending on the gene to be analyzed.

Conditions, states, and phenomena which may cause LOI and may be examined to assess the presence or absence of LOI include: the state or condition of the cellular machinery for DNA methylation, the state of the imprinting control region on chromosome 11, the presence of trans-acting modifiers of imprinting, the degree or presence of histone deacetylation or histone deacetylation, imprinting control center, transacting modulatory factors, changes in chromatin caused by polycomb-like proteins, trithorax-like proteins, human homologues of other chromatin-affecting proteins in other species such as Su(var) proteins in Drosophila, SIR proteins in yeast, mating type silencing in yeast, or XIST-like genes in mammals.

It is also possible to detect LOI by examining the DNA associated with the gene or genes for which the presence or absence of LOI is being assessed. By the term "the DNA associated with the gene or genes for which the presence or absence of LOI is being assessed" it is meant the gene, the DNA near the gene, or the DNA at some distance from the gene (as much as a megabase or more away-i.e., methylation changes can be that far away, since they act on chromatin over long distances). Such approaches include measuring the degree of methylation in the DNA associated with the gene or genes for which the presence or absence of LOI is being assessed. It is also possible to detect LOI by examining modifications to DNA-associated protein, such as histone acetylation and histone deacetylation; changes to binding proteins detected by band shift, protection assays, or other assays, in addition to changes to the DNA sequence itself.

The degree of methylation in the DNA, associated with the gene or genes for which the presence or absence of LOI is being assessed, may be measured by means of a number of analytical techniques. For example, the DNA, associated with the gene or genes for which the presence or absence of LOI is being assessed, may be sequenced using conventional DNA sequencing techniques as described in Current Protocols in Molecular Biology. Asubel et al., Wiley Interscience, 1998, which is incorporated herein by reference. In this case, the biological sample will be any which contains sufficient DNA to permit sequencing.

In addition, the degree of methylation in the DNA, associated with the gene or genes for which the presence or absence of LOI is being assessed, may be measured by fluorescent in situ hybridization (FISH) by means of probes which identify and differentiate between genomic DNAs, associated with the gene for which the presence or absence of LOI is being assessed, which exhibit different degrees of DNA methylation. FISH is described in the *Human chromosomes: principles and techniques* (Editors, Ram S. Verma, Arvind Babu Verma, Ram S.) 2nd ed., New York: McGraw-Hill, 1995, and de Capoa A., Di Leandro M., Grappelli C., Menendez F., Poggesi I., Giancotti P., Marotta, M. R., Spano A., Rocchi M., Archidiacono N., Niveleau A. Computer-assisted analysis of methylation status of individual interphase nuclei in human cultured cells. *Cytometry.* 31:85–92, 1998 which is incorporated herein by reference. In this case, the biological sample will typically be any which contains sufficient whole cells or nuclei to perform short term culture. Usually, the sample will be a tissue sample which contains 10 to 10,000, preferably 100 to 10,000, whole somatic cells.

Typically, in methods for assaying allele-specific gene expression which rely upon the differential transcription of the two alleles, RNA is reverse transcribed with reverse transcriptase, and then PCR is performed with PCR primers that span a site within an exon where that site is polymorphic (i.e., normally variable in the population), and this analysis is performed on an individual that is heterozygous (i.e., informative) for the polymorphism. One then uses any of a number of detection schemes to determine whether one or both alleles is expressed. See also, Rainier et al. (1993) *Nature* 362:747–749; which teaches the assessment of allele-specific expression of IGF2 and H19 by reverse transcribing RNA and amplifying cDNA by PCR using new primers that permit a single round rather than nested PCR; Matsuoka et al. (1996) *Proc. Natl. Acad Sci USA* 93:3026–3030 which teaches the identification of a transcribed polymorphism in p57$^{KIP2}$; Thompson et al. (1996) *Cancer Research* 56:5723–5727 which teaches determination of mRNA levels by RPA and RT-PCR analysis of allele-specific expression of p57$^{KIP2}$; and Lee et al. (1997) *Nature Genet.* 15:181185 which teaches RT-PCR SSCP analysis of two polymorphic sites. Such disclosures are herein incorporated by reference. In this case, the biological sample will be any which contains sufficient RNA to permit amplification and subsequent reverse transcription followed by polymerase chain reaction. Typically, the biological sample will be a tissue sample which contains 1 to 10,000,000, preferably 1000 to 10,000,000, more preferably 1,000,000 to 10,000,000, somatic cells.

It is also possible to utilize allele specific RNA-associated in situ hybridization (ASISH) to detect the presence or absence of LOI by relying upon the differential transcription of the two alleles. In ASISH, the relative abundance of transcribed mRNA for two alleles is assessed by means of probes which identify and differentiate between the mRNA transcribed from the two alleles. Typically, the probes are tagged with fluorescent labels which results in a high sensitivity and easily quantifiable results. ASISH is described in Adam et al. (1996) "Allele-specific in situ hybridization (ASISH) analysis: a novel technique which resolves differential allelic usage of H19 within the same cell lineage during human placental development," *Development* 122:83–47, which is incorporated herein by reference. In this case, the biological sample will typically be any which contains sufficient whole cells or nuclei to perform histological section and in situ hybridization. Usually, the sample will be a tissue sample which contains 10–100,000, preferably 100–1000, whole somatic cells.

According to the present invention, it is also possible to detect LOI by examining allele-specific post-transcriptional effects (i.e., effects after transcription and before translation), like alternate splicing that depends on which allele was transcribed, and detection of secondary structure of the RNA.

It is also possible, according to the present invention, to detect LOI by examining the relative translation of the two alleles of the gene or genes for which the presence or absence of LOI is being measured. In this case, the presence or relative abundance of the two polypeptides arising from the expression of the two alleles is measured directly. This approach can be effected by any known technique for detecting or quantifying the presence of a polypeptide in a biological sample. For example, allele-specific translational effects may be examined by quantifying the proteins expressed by the two alleles using antibodies specific for each allele (transcribed, translated polymorphism). Such effects may be measured and/or detected by such analytical techniques as Western blotting, or use of an ELISA assay. In this case, the biological sample will be any which contains a sufficient amount of the polypeptide(s) encoded by the gene(s) for which the presence or absence of LOI is being measured.

LOI may also be detected by examining post-translational effects, such as secondary modifications that are specific to one allele, like glycosylation or phosphorylation. For example, one allele may be modified, say by phosphorylation or glycosylation, and the other one not. Because the polymorphism encodes a recognition motif, then one can readily distinguish the difference by a Western blot, detecting alternate migration of the polypeptide or protein; use of antibodies specific for the modified form; radioactive incorporation of phosphoryl group or glycosyl group or other modification (i.e., in living cells, followed by the detection of a band at a varying location).

LOI may also be detected by reliance on other allele-specific downstream effects. For example, depending on the metabolic pathway in which lies the product of the imprinted gene; the difference will be 2× versus 1× (or some number in between) of the product, and therefore the function or a variation in function specific to one of the alleles. For example, for IGF2, increased mitogenic signaling at the IGF1 receptor, increased occupancy of the IGF1 receptor, increased activity at the IGF2 catabolic receptor, decreased apoptosis due to the dose of IGF2; for KvLQT1, change in the length of the QT interval depending on the amount and isoform of protein, or change in electrical potential, or change in activity when the RNA is extracted and introduced into Xenopus oocytes.

It is also possible to detect LOI by detecting an associated halotype, i.e., linked polymorphisms that identify people whose genes are prone to LOI.

In the examples described below, LOI's detected by relying on a polymorphism, i.e., a genetic difference between the two alleles. However, it will be recognized that many of the techniques described above may be used to detect LOI even when there is no polymorphism in the two alleles of the gene or genes for which the presence or absence of LOI is being measured. For example, LOI may be detected by reliance on allele-specific DNA methylation (polymorphism independent); histone acetylation; other modifications to DNA; or alterations in replication timing, when the imprinted allele shows "replication timing asynchrony" i.e. the two alleles replicate at different times. When the two alleles replicate at the same time, LOI may be detected by FISH. Since imprinted alleles pair in the late S phase, LOI may be detected by the absence of such pairing in the late S as observed by FISH.

On the other hand certain techniques are more conveniently used when there is a polymorphism in the two alleles of the gene or genes for which the presence or absence of LOI is being measured. For example, RT-PCR followed by SSCP (single strand conformational polymorphism) analysis; restriction enzyme digestion analysis followed by electrophoresis or Southern hybridization; or radioisotopic PCR; PCR; allele-specific oligonucleotide hybridization; direct sequencing manually or with an automated sequencer; denaturing gradient gel electrophoresis (DGGE); and many other analytical techniques can be used to detect LOI when relying on a polymorphism.

The presence or absence of LOI may be determined for any gene or genes which are known to normally exhibit imprinting. Currently there are about 22 genes which are known to be normally imprinted (see Feinberg in *The Genetic Basis of Human Cancer*, B Vogelstein & K Kinzler, Eds., McGraw Hill, 1997, which is incorporated herein by reference). Examples of such penes include, but are not limited to, IGF2, H19, p57$^{KIP2}$, KvLQT1, TSSC3, TSSCS, and ASCL2. However, it is expected that additional genes which normally exhibit imprinting will be discovered in the future and the LOI of such genes may be the target of the present methods and are therefore included in the present invention.

Direct approaches to identifying novel imprinted genes include, but are not limited to, positional cloning efforts aimed at identifying imprinted genes near other known imprinted genes (Barlow et al. (1991) *Nature* 349:84–87); techniques comparing gene expression in parthenogenetic embryos to that of normal embryos (Kuroiwa et al. (1996) *Nat. Genet.* 12:186–190) and restriction landmark genome scanning (Nagai et al. (1995) *Biochem. Biophys. Res. Commun.* 213:258–265).

In a preferred embodiment, the gene or genes for which LOI is detected is selected on the basis of which particular type of cancer is sought to be detected. For example, if the screening test is for the presence of colorectal cancer or the risk of contracting colorectal cancer, it is preferred that the gene for which the degree of LOI is determined is the IGF2 gene. It is contemplated as part of the present invention that other genes may be associated with colorectal cancer or with other types of cancers. It is further contemplated that the present invention includes using the techniques and procedures described herein for the diagnosis, detection or determining the predisposition for other cancers and other diseases.

If the biological sample of the subject in question is found to exhibit LOI, then that subject is identified as having an increased probability of having cancer. In this case, it may be preferred to carry out further diagnostic tests to probe for the possibility of cancer being present in the subject. Examples of such further diagnostic tests include, but are not limited to, chest X-ray, colorectal examination, endoscopic examination, MRI, CAT scanning, or other imaging such as gallium scanning, and barium imaging.

The method of screening for the risk of contracting cancer is carried out much the same as the above-described method for detecting the presence of cancer or other disease with the exception that the detection of LOI in the biological sample of a subject results in the subject as being classified as having an increased risk of contracting cancer or other disease. In this embodiment of the present invention, it may be preferred to perform one or more of the above-described further diagnostic tests to probe for the possibility of cancer being present in the subject. In addition, it may also be preferred to prescribe a schedule for performing additional diagnostic tests in the future, even if no cancer is present at the time LOI is detected. For example, if LOI is detected in a biological sample of a subject and indicates an increased risk of contracting cancer, it may be preferred to schedule periodic (e.g., every 1 to 12 months) chest X-rays, colorectal examinations, endoscopic examination, MRI, CAT scanning, other imaging such as gallium scanning, and/or barium imaging for that subject.

Similarly, according to the present invention, if the biological sample of the subject in question is found to exhibit LOI, then that subject is identified as having an increased probability of having replication repair error defects. In this embodiment of the present invention, it may be preferred to carry out the same further steps as described above in the context of detecting cancer and detecting an increased risk of contracting cancer.

In another preferred embodiment of the present invention testing is performed by measuring the degree of LOI for a particular gene or set of genes. By "the degree of LOI" it is meant the percentage of total expression (as measured by actual expression or transcription) attributable to the allele which is normally imprinted. The degree of LOI may be calculated by allele ratio, i.e., the more abundant allele divided by the less abundant allele. In another embodiment, the degree of LOI may be calculated by the following formula:

$$\text{Degree of } LOI = -\frac{E_i}{E_i + E_n} \times 100 \times 2$$

in which $E_i$ is the level of expression due to the allele which is normally imprinted silenced and $E_n$ is the level of expression due to the allele which is normally imprinted expressed. Thus, the degree of LOI may be determined by any method which allows the determination of the relative expressions of the two alleles. For example, a degree of LOI of 100% reflects complete LOI (equal expression of both alleles), while a degree of LOI of 0% reflects no LOI (expression of only one allele). Any method of measuring the relative expression of the two alleles is considered to be included in the present invention.

In a particularly preferred embodiment of the present invention, the degree of LOI is measured for the IGF2 gene when screening for the presence of colorectal cancer. In another particularly preferred embodiment of the present invention, the degree of LOI is measured for the IGF2 gene when screening for the presence of stomach cancer. In another particularly preferred embodiment of the present invention, the degree of LOI is measured for the IGF2 gene when screening for the presence of esophageal cancer. In another particularly preferred embodiment of the present invention, the degree of LOI is measured for the IGF2 gene when screening for the presence of leukemia.

According to the present invention, a number of the techniques described above in the context of detecting LOI may also be used effectively to measure the degree of LOI. For example, the degree of LOI may be easily quantified by means of such techniques as, e.g.:

1. Measuring the alterations in DNA directly including, but not limited to, methylation, histone acetylation, etc. by, for example, FISH;
2. Measuring the degree of relative transcription by ASISH; RNA in situ hybridization to metaphase chromosomes;
3. Measuring the degree of relative transcription by RT-PCR of mRNA followed by a variety of detection schemes;
4. Measuring the degree of relative translation by Western blotting, ELISA, etc.; and
5. DNA in situ hybridization to metaphase or interphase chromosomes when change in replication timing, allele pairing, or secondary structure can be detected.

When measuring the degree of LOI quantitatively by relying on the relative levels of transcription of the two alleles using quantitative PCR amplification, it is important to obtain high quality RNA. In this case, it is preferred to place the tissue in an appropriate buffer and take those precautions known to and used by those of ordinary skill in the art when isolating RNA. Such techniques are described in Current Protocols in Molecular Biology, Asubel et al., Wiley Interscience, 1998, which is incorporated herein by reference in its entirety.

When assessing the degree of LOI quantitatively by a method which relies on the relative transcription of the two alleles, using quantitative PCR amplification, it is also important to avoid genomic DNA contamination of the cDNA, which is obtained from the mRNA. In addition, it is important to ensure linear amplification during any amplification step, e.g., polymerase chain reaction (PCR) amplification of the cDNA obtained from the mRNA. If the primers used in such a PCR amplification are exhausted, it is possible to obtain heterodimers of two different alleles, and any subsequent restriction enzyme digestion will not reflect the true ratio of expression of the two alleles. For example, if alleles are a and b, and the corresponding cDNAs are a' and b', and the restriction enzyme being used recognizes allele b, then the restriction enzyme cuts the bb' double helix. However, if the PCR amplification is allowed to progress to the point where the primers are exhausted, it is possible to obtain after the final annealing and extension a mixture of aa', ab', ba', and bb' rather than the desired mixture of aa' and bb', since alleles a and b may differ by only a small number of nucleotide residues. The restriction enzyme may then cut only bb' without cutting ab' and ba' resulting in a false apparent 3:1 ratio of expression.

It is also preferred to use a linear detection platform. In this regard, good results have been achieved by using a PhosphorImager (model 445SI, manufactured by Molecular Dynamics) which detects radioactive emissions directly from a gel. Other linear detection systems include carefully titrated autoradiography followed by image analysis, beta-emission detection analysis (Betascan). Another linear detection platform is an automated DNA sequencer such as ABI 377 analyzer.

It is important to note that, although in the Examples provided below the presence of a polymorphism in the gene of interest formed the basis for measuring the degree of LOI, as in the case of detecting LOI, it is also possible to assess the degree of LOI in a particular gene even when no polymorphism is present in that gene. For example, imprinting can be assessed by the degree of methylation of CpG islands in or near an imprinted gene (e.g., Barletta, *Cancer Research*, op. cit). In addition, imprinting can be assessed by changes in DNA replication timing asynchrony, e.g. White L M, Rogan P K, Nicholls R D, Wu B L, Korf B. Knoll J H, Allele-specific replication of 15q11–q13 loci: a diagnostic test for detection of uniparental disomy. *American Journal of Human Genetics.* 59:423–30, 1996.

On the other hand, certain techniques are more conveniently used when there is a polymorphism in the two alleles of the gene or genes for which the presence or absence of LOI is being measured. For example, RT-PCR, followed by gel electrophoresis to distinguish length polymorphisms, or RT-PCR followed by restriction enzyme digestion, or by automated DNA sequencing, or by single strand conformational polymorphism (SSCP) analysis, or denaturing gradient gel electrophoresis, etc.; or, completely DNA based methods that exploit, for example DNA methylation (then there is no RT step, to convert RNA to cDNA prior to PCR).

Once the degree of LOI has been measured for the gene or genes in question, the risk of having cancer is then assessed by comparing the degree of LOI for that gene or genes is to a known relationship between the degree of LOI and the probability of the presence of the particular type of cancer or other disease. The relationship between the degree of LOI and the probability of the presence of a particular type of cancer may be determined for any combination of a normally imprinted gene or genes and a particular type of cancer by determining.

The method of screening for the risk of contracting cancer is carried out much the same as the above-described method for detecting the presence of cancer with the exception that the measured degree of LOI is compared to a known relationship between the degree of LOI and the probability of contracting the particular type of cancer. The relationship between the degree of LOI and the probability of contracting a particular type of cancer may be determined by one of ordinary skill in the art for any combination of a normally imprinted gene or genes and a particular type of cancer by determining the degree of LOI in a statistically meaningful number of tissue samples obtained from patients with cancer, and determining the degree of LOI in a statistically meaningful number of tissue samples obtained from patients without cancer, and then calculating an odds ratio as a function of the degree of LOI.

It should also be understood that the present methods of detecting cancer, assessing the risk of contracting cancer, and assessing the risk of having replication error repair defects may be carried out by comparing the degree of LOI against one or more predetermined threshold values, such that, if the degree of LOI is below a given threshold value then the subject is assigned to a low risk population for having cancer, contracting cancer, and/or having replication error repair defects. Alternatively, the analytical technique may be designed not to yield an explicit numerical value for the degree of LOI, but instead yield only a first type of signal when the degree of LOI is below a threshold value and/or a second type of signal when the degree of LOI is below a threshold value. It is also possible to carry out the present methods by means of a test in which the degree of LOI is signaled by means of a non-numeric spectrum such as a range of colors encountered with litmus paper.

The present methods of detecting the presence of a disease, assessing the risk of contracting a disease, and detecting the risk of having replication may suitably be carried out on any subject selected from the population as a whole. However, it may be preferred to carry out this method on certain selected groups of the general population when screening for the presence of particular types of cancer. Preferably, the present method is used to screen selected groups which are already known to have an increased risk of contracting the particular type of cancer in question.

It is to be understood that the present invention can be performed on the general population to assess the presence or risk of disease. In another embodiment of the present invention, target patients may be tested to detect a particular type of disease, for example colon cancer. In addition, according to the present invention, subgroups of those patients who already are thought to be at some increased risk, such as e.g., a weak family history, may be tested.

In another embodiment, the present invention includes kits which are useful for the detection of cancer and/or assessing the risk of contracting cancer. According to the present invention, the kits contain those components, ingredients, and/or means for carrying out the present methods. The components contained in the kit depend on a number of factors, including: the condition, state, or phenomenon relied on to detect LOI or measure the degree of LOI, the particular analytical technique used to detect LOI or measure the degree of LOI, and the gene or genes for which LOI is being detected or the degree of LOI is being measured.

In the embodiment of the present invention wherein LOI is detected by relying on the degree of methylation of the genomic DNA associated with the gene(s) for which LOI is being detected or the degree of LOI is being measured using FISH, the kit will typically contain one or more probes which can identify a specific imprinted gene or group of genes. Typically, such probes will be nucleic acids or monoclonal antibodies and will be linked to, for example, a fluorescent label.

In the case of detecting LOI by relying on the differential rates of transcription of two ploymorphic alleles, the kit may comprise:

(i) means for the amplification of the mRNAs corresponding to the two polymorphic alleles of the gene in question. Examples of such means include suitable DNA primers for the PCR amplification of the mRNAs corresponding to the two polymorphic alleles of the gene in question. Specific examples of such means includes any pair of DNA primers which will anneal to and amplify any gene which is normally imprinted and in which a polymorphism is present.

According to the present invention, the kit may further comprise:

(ii) means for identifying the products of the amplification of the mRNAs corresponding to the two polymorphic alleles of the gene in question.

Such means include, but are not limited to, a restriction enzyme which specifically cleaves one of the products of the amplification of the mRNAs corresponding to the two polymorphic alleles of the gene in question. Specific examples of such enzymes include, but are not limited to, Apa I in the case of the IGF2 gene.

In the embodiment of the present invention wherein the degree of LOI is measured by relying on the differential rates of transcription of two polymorphic alleles, the kit may comprise:

(i) means for the linear amplification of the mRNAs corresponding to the two polymorphic alleles of the gene in question. Examples of such means include a sufficient quantity of suitable DNA primers for the PCR amplification of the mRNAs corresponding to the two polymorphic alleles of the gene in question, such that the PCR amplification may be carried out without exhausting the primers and linear amplification achieved. Specific examples of such means includes any pair primers for any gene which is normally imprinted.

According to the present invention, the kit may further comprise:

(ii) means for identifying the products of the amplification of the mRNAs corresponding to the two polymorphic alleles of the gene in question. Such means include a restriction enzyme which specifically cleaves one of the products of the amplification of the mRNAs corresponding to the two polymorphic alleles of the gene in question.

When detecting LOI or measuring the degree of LOI by ASISH, the kit will typically contain one or more probes which can identify and distinguish between the RNA associated with the two alleles. Typically, such probes will be nucleic acids that are specific for each allele, and are used either sequentially or together using different fluorescent labels for each allele.

When detecting LOI or measuring the degree of LOI by assessing the relative translation of two alleles, the kit may contain antibodies that distinguish the protein product of the two alleles.

In another embodiment of the present invention, a method for screening infants/newborns is provided for the risk of SIDS. In this embodiment, the imprinting pattern of a tissue sample of a newborn is examined. Detection of an abnormal imprinting pattern in the tissue sample indicates that the infant/newborn is at risk from SIDS. The tissue sample of the infant/newborn is preferably blood, and the detection of the imprinting pattern in the tissue may be determined for any of the genes discussed above. It preferred that the imprinting pattern be determined for KvLQT1. KvLQT1 is normally imprinted in all tissues except the heart. Detection of an abnormal imprinting pattern for KvLQT1 will result in that infant/newborn being categorized as being at risk from SIDS. When an infant/newborn is so categorized, it may be preferred to carry out further steps such as prescribing nocturnal monitoring, etc.

Other features of the invention will become apparent in the course of the following descriptions of exemplary embodiments which are given for illustration of the invention and are not intended to be limiting thereof.

EXAMPLE 1

Material

Eighty specimens derived from colorectal cancer patients were analyzed for the presence of heterozygosity of either of either an Apa I or CA repeat polymorphism in exon 9 of the human IGF2 gene (Rainier et al. (1993) *Nature* 362:747–749) that can be used to assess allele-specific expression by reverse transcription polymerase chain reaction (RT-PCR), of which 27 were heterozygous and thus informative for imprinting status analysis. Sixteen informative of 47 normal colon samples were used as controls. Fifteen informative of 40 peripheral blood samples were further examined for IGF2 imprinting status. There were no significant differences between the cancer and noncancer patients for age, race, or sex. (FIG. 1)

Nucleic Acid Preparation:

DNA and RNA were extracted from snap-frozen tissues and peripheral blood leukocytes. For DNA, tissues or cells were incubated at 55° C. overnight in a lysis buffer containing 1×TE, 0.5% SDS, 150 mM NaCl and 100 $\mu$g/ml proteinase K, followed by extraction with phenol/chloroform and ethanol precipitation. RNA was extracted with RNAzol B (Tel-test) following the manufacturer's instructions.

Quantitative Analysis of IGF2 Imprinting Status:

As described in the Results, many samples demonstrated substantial although incomplete loss of imprinting. A quantitative PCR assay (relative to the two alleles) was developed (also see FIG. 1). RNA samples were treated with DNase prior to making any cDNA, in order to avoid any possible genomic DNA contamination. The reaction was performed in a 25 $\mu$l volume, using 10 $\mu$l RNA (5–10 $\mu$g), 5 $\mu$l 5× transcription buffer (Promega), 0.7 $\mu$l RNasin (Promega), and 2 $\mu$l RNase-free DNase I (Boehringer-Mannheim), at 25° C. for 30 min. The DNase I was inactivated at 70° C. for 10 min. The RNA was extracted with phenol/chloroform and chloroform sequentially, and then ethanol-precipitated together with 20 pmol of RT primer P10 in exon 9. cDNA was generated in a 25 $\mu$l reaction containing 5 $\mu$l 5X RT buffer (LTI), 2.5 $\mu$l dNTP (10 mM), 0.7 $\mu$l RNasin (Promega), 2.5 $\mu$l sodium pyrophosphate (40 mM), and 2 $\mu$l AMV reverse transcriptase (LTI), at 42° C. for 1 hour. The enzyme was inactivated at 65° C. for 15 min. As a control, all reactions were performed in duplicate in the presence and absence of reverse transcriptase. Either the Apa I or $(CA)_n$ repeat polymorphism was used to analyze imprinting status of the gene. To exclude any possibility of genomic DNA contamination, PCR across an intron-exon boundary was first performed. For the Apa I polymorphism, primer Pla, located on exon 8, and primer P8b, on exon 9, were used to amplify cDNAs derived from reverse transcription. PCR was performed using the following conditions: 50 µl of reaction volume containing 2 µl of cDNA template, at a final concentration of 0.5 FM each primer, 0.15 mM of dNTP, 1.5 mM of MgCl$_2$, 1×PCR buffer (LTI), and 1.5 U of Taq polymerase (LTI). Thermal cycling was performed as follows: 94° C. for 2 minutes; 32 cycles at 94° C. for 1 minute, 52° C. for 1 minute, 72° C. for 1.5 minutes; and 72° C. for 10 minutes. The PCR-amplified products were purified from 1.5% agarose gels, using a 123 bp ladder to identify the location of the cDNA (1224 bp as distinguished from genomic DNA at 1513 bp). This additional step made any genomic DNA contamination impossible. The cDNA fragments were purified using the Qiaquick gel extraction kit (Qiagen). A second round of PCR amplification was then performed using 1 µl of purified first round PCR product as template, and primers P2 and P3, with P3 previously labeled using [γ$^{32}$P-ATP. The second round of PCR amplification was followed by 35 cycles of 94° C. for 30 sec.; 55° C. for 40 sec.; 72° C. for 1.5 min.; and 72° C. for 10 min. The PCR product (10 µl) was digested in a 20 µl volume with 20 U Apa 1, 10 mM NaCl, 3 mM MgCl$_2$, pH 7.5, and electrophoresed on a 6% denatured polyacrylamide gel. The (CA)$_n$ repeat region was analyzed using primers P8 and labeled P9, and visualized directly on a 6% denatured polyacrylamide gel. Each allele was then quantified on a Phorphorlmager (Molecular Dynamics), as percent of the less abundant allele (0% representing monoallelic expression, 100% representing equal biallelic expression). Primers were maintained in excess over PCR product to avoid heterodimer formation. Control mixing experiments confirmed equal amplification of the two alleles, and the absence of heterodimer formation in the Apa I assay. Samples were analyzed in duplicate with an assay to assay variation of 0–10%, and the results for each sample were averaged. Statistical analysis among the various groups revealed significant quantitative differences, as described in the Results. This analysis allowed us to define a threshold level for partial LOI as 50% (i.e., <3:1 ratio of the more abundant to less abundant allele). Primer sequences were as follows:
P1a, 5'-ATCGTTGAGGAGTGCTGTTTC-3' SEQ ID NO: 1;
P2, 5'-CTTGGACTTTGAGTCAAATTGG-3 SEQ ID NO: 2;
P3, 5'-GGTCGTGCCAATTACATTTCA-3' SEQ ID NO: 3;
P8, 5'-CTCATACTTTATGCATCCCCG-3' SEQ ID NO: 4;
P8b, 5'-CGGGGATGCATAAAGTATGAG-3' SEQ ID NO: 5;
P9, 5'-GCCTGATCCATACAGATATCG-3' SEQ ID NO: 6;
P10, 5'-GCATCTCTGTCATGGTGGAAAG-3' SEQ ID NO: 7.

Promoter-Specific Allele Usage Analysis:

IGF2 specific cDNA was made as described above. A semi-nested PCR approach was performed using promoter-specific primers to amplify transcripts derived from specific promoters as described previously (He and Cui, 1998). Duplicate PCR products were separated on 1.5% agarose gels, and the DNA fragments migrating at the predicted specific cDNA size were isolated and purified. Southern blot hybridization was then performed using allele-specific oligonucleotide probes that discriminated the Apa I within exon 9 of IGF2. The conditions for Southern allele-specific hybridization (SASH) were as follows: oligonucleotide probes were prepared by 3' end-labeling with $^{32}$P-dATP and purification as described previously (Cui 1997). The filter was hybridized at 45° C. overnight, followed by stringent washing using 0.1 SSC/0.1% SDS at 55° C., for 10 minutes for oligonucleotide probe A (without the Apa I site) and 5 minutes for probe B (with Apa I site). A reconstitution experiment was done in parallel to ensure accurate quantitation. Oligonucleotide probe sequences were: probe A, 5'-TGTGATTTCTGGGGTCCTTCTTTTCTCTT-3 SEQ ID NO: 8, probe B, 5'-TGTGATTTCTGGGGCCCTTCT TTT CTCTT-3' SEQ ID NO: 9.

DNA Microsatellite instability Analysis

DNA microsatellite instability is assessed by comparing tumor and matched normal genomic DNA, using the following 15 microsatellite markers for each sample: BAT-25, BAT-26, D2S123, D11S1318, D17S250, AP2, D11OS89, AP3, D18S58, D3S1283, D11S904, D11S1758, D11S4124, D11S860, and APC. PCR amplification was performed using 1 µl of DNA (=0.15 µg) in a final volume of 10 µl, with a final concentration of 0.1 µM each primer, 0.15 mM dNTP, 1.5 mM MgCl$_2$, 1× PCR buffer (LTI), and 0.06 U Taq polymerase. In each case, one primer was end-labeled. PCR products were analyzed on 6% denatured polyacrylamide gels. The primer sequences were as described previously (Dietmaier et al. (1997) *Cancer Res.* 57:4749–4756) (Genome Database, Johns Hopkins University, http://Hgdb.www.gcb.org).

Statistical Analysis:

Cross-tabulation and comparison of sample means were used to identify differences between colon cancers and normal mucosa with and without LOI, between samples with and without microsatellite instability, and to examine differences in the characteristics of cancer patients with and without LOI. Where appropriate, the chi-square test of independence and student's t-test were applied to the data to determine significant differences. Quantitative LOI was compared between cancers and matched normal mucosa using a paired sample t-test.

EXAMPLE 2

LOI in colorectal cancers and matched normal mucosal samples

Figure 2A:
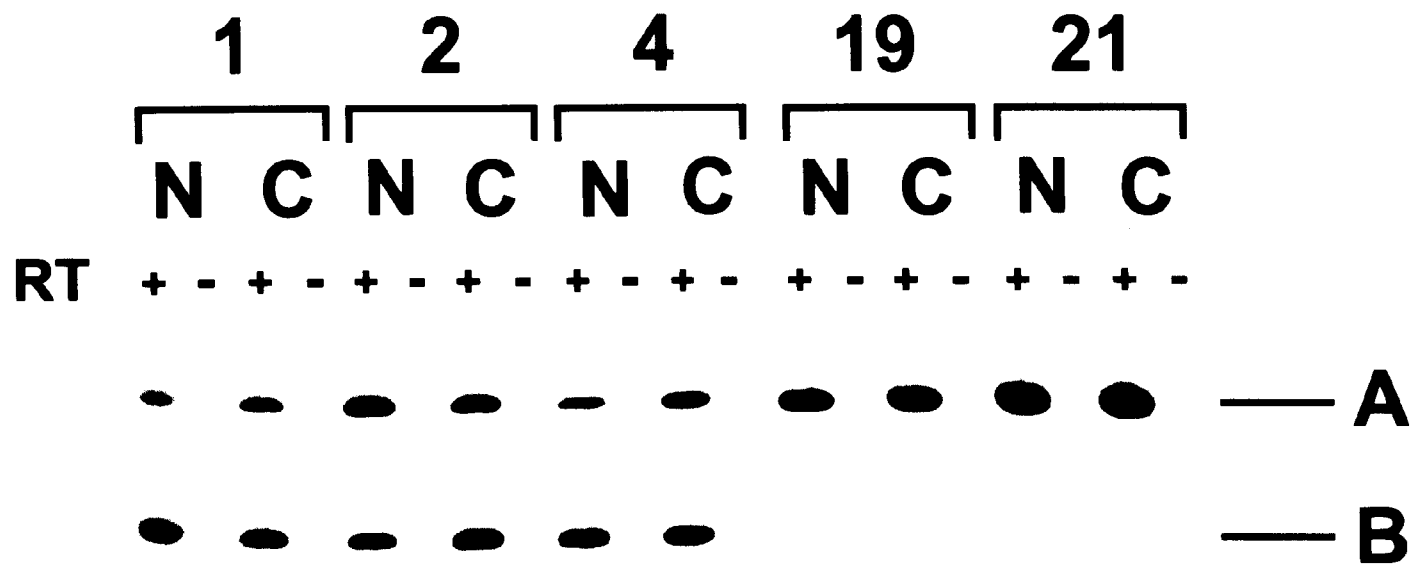
Figure 2B:
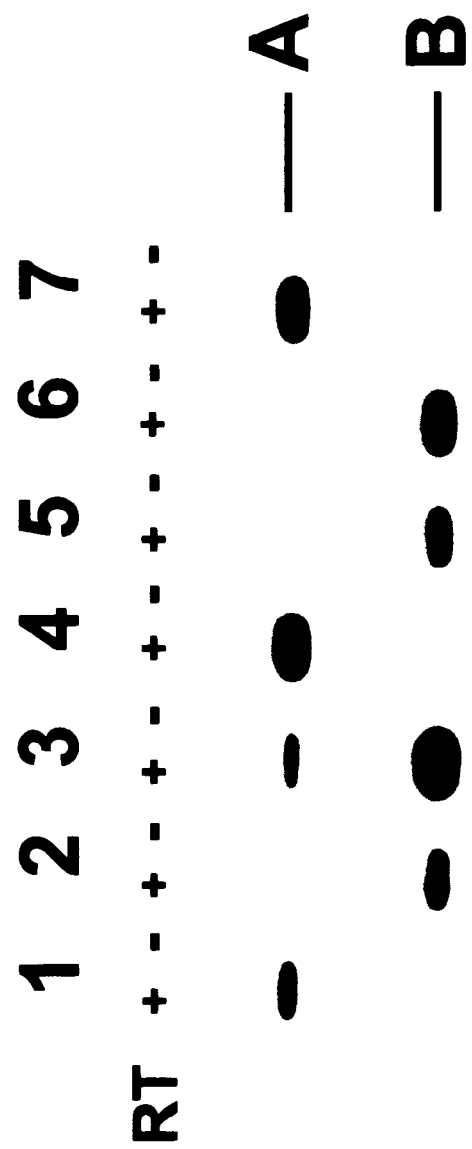

Of the 27 tumors informative for IGF2, 12 (44%) showed substantial expression of the less abundant allele (LOI was defined as <3:1 ratio of the more abundant to less abundant allele). Surprisingly, in all 10 cases in which the tumor showed LOI and matched normal colonic mucosa was available from the same patient, the matched normal tissue also exhibited LOI (FIG. 2A; patients 1, 2, 4). In contrast, only 1 of 12 (8.5%) matched normal mucosal specimens showed LOI when the matched tumor did not show LOI (FIG. 2A; patients 19, 21). This difference was highly statistically significant (p <0.001).

Figure 3:
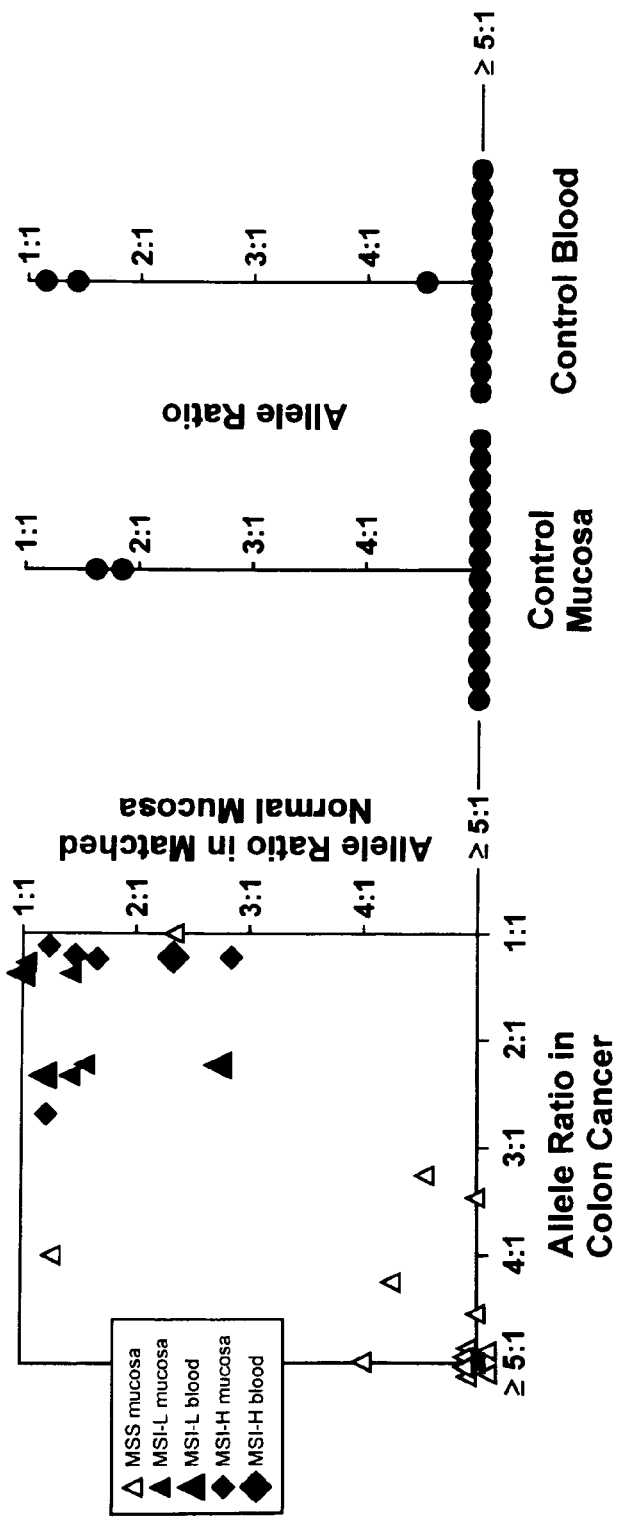
FIG. 3 shows the link between LOI in colorectal cancer, LOI in matched normal mucosa, and microsatellite instability. Paired tumor-normal samples show a strong correlation between LOI in the cancer and LOI in matched normal mucosa, expressed as the ratio of the more abundant to less abundant allele. LOI also distinguishes patients with and without MSI in their tumors.

To avoid any arbitrariness in scoring LOI, the quantitative level of LOI of each tumor was compared to that of the matched normal mucosa of each patient. The degree of LOI in the tumor correlated strongly with the degree of LOI in matched normal tissue (FIG. 3; $r^2$=0.757, p<0.001). A paired student's t-test also showed no significant difference between the degree of LOI in the paired tumor and normal specimens. LOI in matched normal mucosa was not due to contaminating tumor cells, because in every case, the matched normal tissue was derived from the colon>10 cm from the tumor, and the normal specimens were all verified to be free of tumor, dysplasia, or any other histopathological abnormality. Thus, LOI was a property of the colon itself in most patients with LOI, affecting both the normal mucosa and the cancer.

EXAMPLE 3
No change in promoter usage in tumors with LOI

Figure 4:
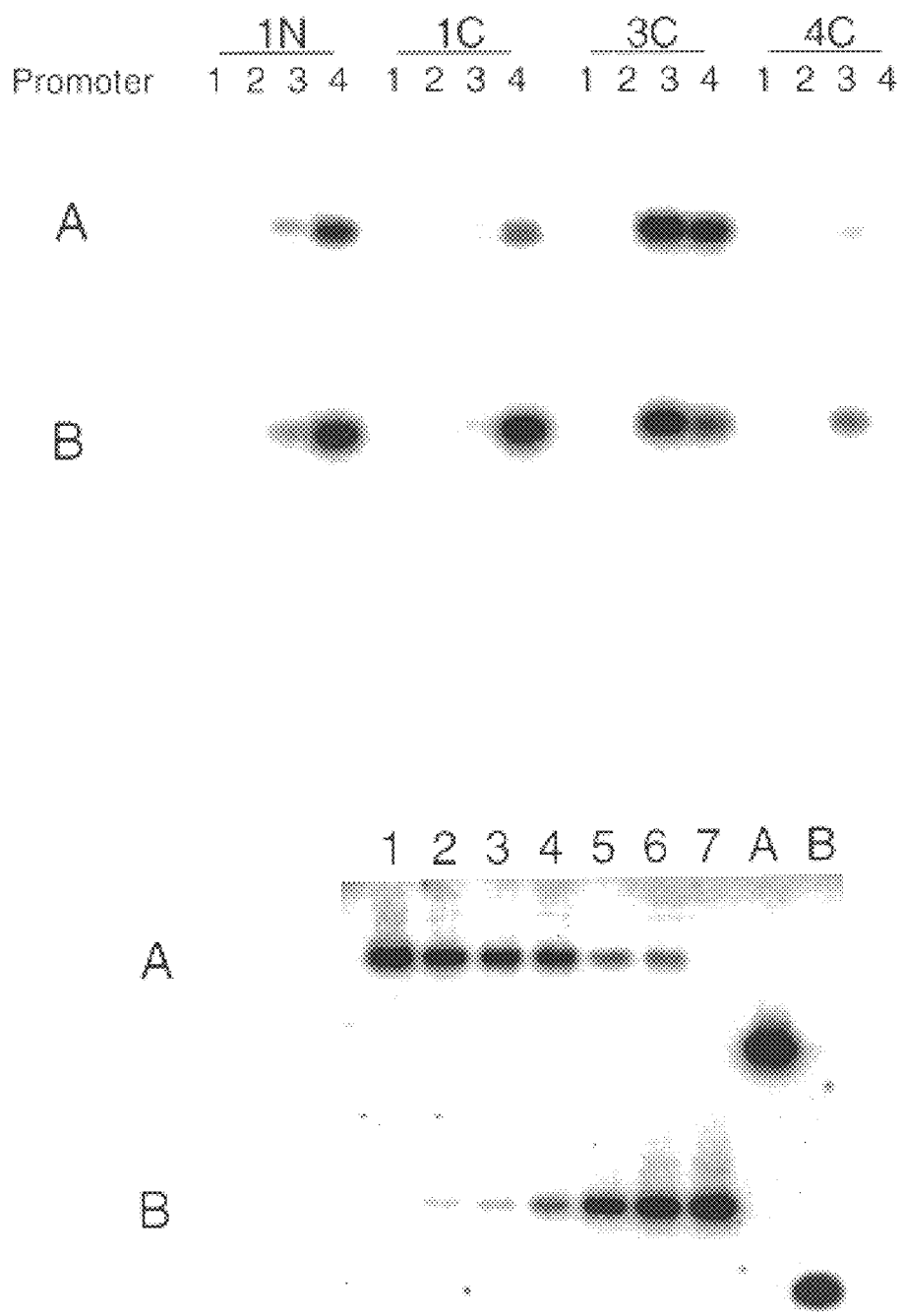
FIG. 4 shows the analysis of promoter-specific imprinting in colon cancer patients. 3(A) Gene-specific cDNA, derived from reverse transcription with an IGF2 downstream primer, was amplified using promoter-specific primers. PCR products were subjected to Southern allele-specific hybridization (SASH) using allele-specific oligonucleotide probes, as described previously (He et al. (1998) *Oncogene* 16:113–119 which is incorporated herein by reference). Note that promoters 3 and 4 clearly displayed biallelic expression in all samples examined, while expression from promoters 1 and 2 was not detectable. 3(B) A reconstitution control was performed concurrently, by mixing cDNA homozygous for the A and B alleles at varying ratios, and then amplifying with promoter 4-specific primers. PCR products were detected by allele-specific oligonucleotide probe A or B respectively. The assay demonstrated that the amplification of promoter-specific cDNA was linear and quantitative for both alleles under the conditions used.

The IGF2 gene contains four promoters, P1–P4, and only P2–P4 are normally imprinted. To confirm that biallelic expression was due to LOI and not to a shift in promoter usage to P1, promoter-specific RT-PCR was performed, using exon-specific primers (exon 3 for PI, exon 4 for P2, exon 5 for P3, and exon 6 for P4). The PCR products were then analyzed using allele-specific oligonucleotides as described (He et al. (1998) Oncogene 16:113–119), with reconstitution controls performed in parallel. In every case tested, biallelic expression in both tumor and normal specimens was observed from P3 and P4, which are both normally imprinted, and not from PI (FIG. 4). Thus, biallelic expression in both tumor and matched normal specimens reflected abnormal imprinting, rather than a shift in promoter usage.

This result is in contrast to that of Issa et al., who reported expression from the adult P1 promoter in colon cancer, and not from the imprinted promoters P2–P4 (Issa et al. (1996) Proc. Natl. Acad. Sci. USA 93:11757–11762). However, that group examined cell lines rather than primary tumors, and it has been shown directly that there is promoter-specific LOI from P3 and P4 in primary colon cancers examined directly.

EXAMPLE 4
LOI linked to microsatellite instability

Of the 27 informative cancers, 10 showed replication errors of at least two of 15 microsatellite markers tested. Tumors showing microsatellite instability showed a mean expression of the less abundant allele of 39.5%, compared to 16.9% for the cancers without microsatellite instability, a statistically significant difference (p<0.001). These results were essentially the same if tumors with only one microsatellite instability were included, as there was only one such additional tumor. Similarly, matched normal tissues corresponding to tumors with microsatellite instability showed a mean expression of the less abundant allele of 40.4%, compared to 13.2% for the matched normal tissues corresponding to the tumors without microsatellite instability (p <0.001). When the two groups were compared with regard to <3:1 ratio of more abundant allele to less abundant allele (the recommended threshold for substantial LOI), the results were again statistically significant. Of the 10 cases with microsatellite instability of at least two markers, all 10 exhibited substantial LOI (100%; Table 1). In contrast, only 2 of 16 (12.5%) tumors without microsatellite instability showed LOI above this threshold (p<0.001; Table 1). Thus, LOI was specifically associated with microsatellite instability in the tumors. Similarly, all 9 (100%) of the matched normal mucosal specimens corresponding to tumors with two or more microsatellite instability showed LOI, compared to 14% (²⁄₁₄) matched normal mucosal specimens corresponding to tumors without microsatellite instability (p<0.001; Table 1).

The presence of LOI was also significantly associated with the quantitative number of microsatellite instability among the 15 markers tested. The mean number of microsatellite instability among tumors with LOI was 4.7±1.2, compared to 0.07±0.07 for the tumors without LOI (p <0.001). Thus, both subtle and substantial defects in replication error repair were linked to LOI in the colon.

EXAMPLE 5
LOI in Patients without known cancer

These data suggest that LOI in the normal colonic mucosa identifies a subset of patients who show LOI in their cancers, and that this subgroup frequently exhibits MSI in their tumors. If that is the case, then the frequency of LOI in a population of patients without cancer should be similar to the frequency of LOI in the matched normal mucosa of patients who did not show LOI in their tumors. To test this hypothesis, 47 normal colon mucosal specimens were obtained from patients who did not have cancer, of which 16 were informative for IGF2. While many of these specimens showed very low levels of expression of the less abundant allele, only 2 (12.5%, Table 1) showed a <5:1 ratio of allele-specific expression (both <2:1), the same proportion seen in the matched normal mucosa of patients whose tumors did not show MSI (FIG. 4).

Figure 5:
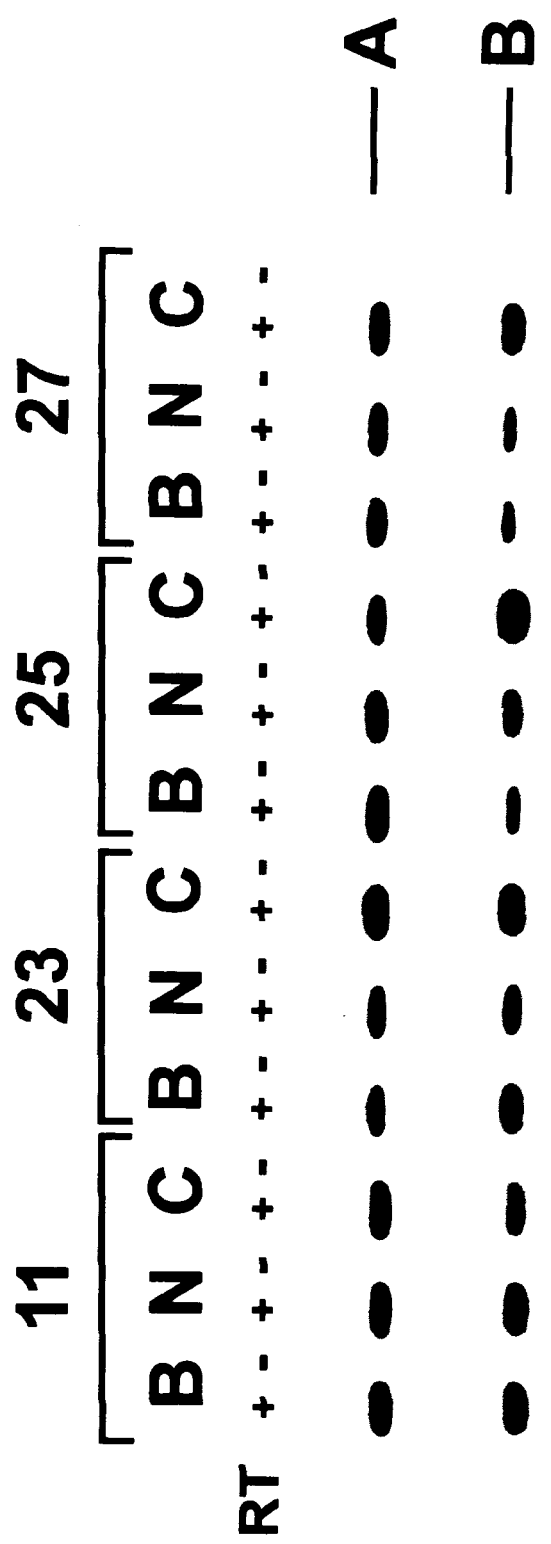
FIG. 5 shows the loss of imprinting in blood, colonic mucosa, and tumor of colon cancer patients. LOI is seen in blood (B), matched normal colonic mucosa (M), and cancer (C) of colon cancer patients 11, 23, 25, and 27. All four patients showed microsatellite instability in their tumors.

In addition, the presence of LOI in the normal colon of colon cancer patients with LOI in their tumors suggests that this abnormality may be present ubiquitously in at least some of these patients. To test this hypothesis, four blood specimens were obtained from patients with LOI in their tumors and normal colon, and all four showed LOI (FIG. 4, FIG. 5). As a control, 40 blood specimens were obtained from a general hospital chemistry laboratory, of which 15 were informative for IGF2, and only 2 of these unselected specimens exhibited substantial or complete LOI (13.3%, p<0.01), similar to the proportion seen in the normal mucosa of noncancer patients. These data suggest that, at least in some patients, abnormal imprinting may be detected in the blood of cancer patients. The results of these Examples are summarized in Table I.

TABLE I

|  | LOI in Normal Colon | | No LOI in Normal Colon | | |
| --- | --- | --- | --- | --- | --- |
|  | Cancer | Matched Normal | Cancer | Matched Normal | P |
| % Expression of less abundant allele | 39.5 ± 7.0 | 40.4 ± 6.1 | 16.9 ± 14.1 | 13.3 ± 11.9 | <0.001 |
| % With replication errors | 91 | NA | 11 | NA | <0.001 |
| Mean # markers with replication errors | 4.7 | NA | 0.07 | NA | <0.001 |
| Age | 48.7 ± 5.5 | | 62.9 ± 4.5 | | <0.01 |
| Sex | 5 M, 6 F | | 8 M, 8 F | | N.S. |
| Race |  |  |  |  | N.S. |
| % in stage 3–4 | 45 | NA | 50 | NA | N.S. |
| % at proximal location | 44 | NA | 50 | NA | 0.6 |

Summary

According to the present invention, it has been determined that there exists frequent loss of imprinting (LOI) in colon cancer, and in the matched normal colonic mucosa of the same patients, as well as in blood samples of 4 patients. This study has two major implications. First, it represents the first genetic abnormality detected at high frequency in the normal tissue of cancer patients in the general population. It is not known whether LOI develops concurrently with the cancer or precedes the development of the cancer. This question will require prospective studies both before and after cancer diagnosis. However, the fact that cancer patients with LOI in their normal mucosa developed cancer on average 14 years younger than those without LOI, suggests that LOI precedes the cancer.

Second, these results demonstrate directly a link between abnormal genomic imprinting and DNA replication errors, because LOI in both normal and cancer tissue was linked both qualitatively and quantitatively to MSI in the tumors.

Imprinted chromosomal regions show asynchronous replication between the two parental chromosomes over a relatively large (several megabase) region (Kitsbert et al. (1993) *Nature* 364:459–463). Furthermore, the two parental homologues are physically associated in late S phase (LaSalle, J M and Lalande, M. (1996) *Science* 272:725–728). LOI does not necessarily detect mutations in conventional HNPCC genes that cause instability in a high proportion of microsatellite markers, as not all tumor cell lines from HNPCC patients show LOI. Rather, it is hypothesized that the altered imprinting described here and the common non-HNPCC related MSI with which it is associated, are due to disturbances in chromatin that affect both replication and imprinting fidelity.

These results help to resolve a paradox in studies of MSI in colorectal cancer. The frequency of MSI in sporadically occurring tumors is 15–37%, approximately half with MSI-H and half with MSI-L. However, germline mutations in genes known to cause MSI are seen in <2% of colon cancer patients, and in only 16% of sporadic tumors with MSI-H and almost none with MSI-L. Thus it has been unclear whether most of the patients with these tumors develop mutations in DNA repair genes in somatic cells during the progression of the tumor, or whether most of these errors are due to as yet unknown germline mutations. The data presented here suggest that MSI precedes the development of cancer. This has an important practical implication, as the traditional assays for MSI require a clonal cell population (a tumor) to compare to a normal cell population, whereas the assay of LOI does not.

Slightly more than 10% of patients in the general population, not known to have cancer, also showed LOI in normal colonic mucosa and in blood. These patients may have cancer or are at substantially increased risk of cancer, since LOI was specifically associated with MSI in colorectal cancer. MSI in many common tumors, including those of the stomach, colon, and lung, is associated with a younger age, positive family history, and/or less accessible and detectable location, suggesting that a relatively large subgroup of cancer patients in the general population are at increased risk of cancer and show MSI in their tumors, even though they do not fall within a well-defined syndrome. Some of the patients with LOI in normal tissue are therefore also at risk for cancers other than colorectal cancer, since MSI-L may be more strongly associated with familial and/or younger onset lung and stomach cancer than with colorectal cancer.

Finally, the assay of genomic imprinting described here is of considerable practical importance, as this assay does not require tumor tissue. The approach described here also represents the first genetic test that ascertains a substantial fraction of patients in the general population with cancer or at risk of cancer.

It should be understood that the foregoing relates only to a preferred embodiment of the present invention and that numerous modifications or alterations may be made therein without departing from the spirit and the scope of the invention as set forth in the appended claims.

What is claimed is:

1. A method for detecting the presence of a disease in a subject, comprising:
   obtaining a normal biological sample from the subject, the normal biological sample being free of histopathological abnormality; and
   screening said normal biological sample for abnormal imprinting in at least one gene wherein abnormal imprinting indicates presence of the disease.

2. The method of claim 1, wherein the disease is cancer, birth defects, mental retardation, obesity, gross motor disturbances, diabetes, or gestational diabetes.

3. The method of claim 2, wherein said cancer is colorectal cancer, esophageal cancer, stomach cancer, leukemia/lymphoma, lung cancer, prostate cancer, uterine cancer, breast cancer, skin cancer, endocrine cancer, urinary cancer, pancreatic cancer, other gastrointestinal cancer, ovarian cancer, cervical cancer, head cancer, neck cancer, or adenomas.

4. The method of claim 2, wherein said cancer is colorectal cancer.

5. The method of claim 2, wherein said at least one gene is IGF2, H19, p57$^{KIP2}$, KvLQT1, TSSC3, TSSC5, or ASCL2.

6. The method of claim 2, wherein said at least one gene is IGF2.

7. The method of claim 2, wherein said normal biological sample is cells from blood, colon, colonic mucosa or tissue.

8. The method of claim 2, comprising measuring the degree of LOI for at least one gene in said normal biological sample.

9. A method for assessing the risk of contracting a disease in a subject, comprising:
   obtaining a normal biological sample from the subject, the normal biological sample being free of histopathological abnormality; and
   screening said normal biological sample for abnormal imprinting in at least one gene wherein abnormal imprinting indicates a risk for contracting the disease.

10. The method of claim 9, wherein said cancer is colorectal cancer, esophageal cancer, stomach cancer, leukemia/lymphoma, lung cancer, prostate cancer, uterine cancer, breast cancer, skin cancer, endocrine cancer, urinary cancer, pancreatic cancer, other gastrointestinal cancer, ovarian cancer, cervical cancer, head cancer, neck cancer, or adenomas.

11. The method of claim 10, wherein said cancer is colorectal cancer.

12. The method of claim 9, wherein said at least one gene is IGF2, H19, p57$^{KIP2}$, KvLQT1, TSSC3, TSSC5, or ASCL2.

13. The method of claim 9, wherein said at least one gene is IGF2.

14. The method of claim 8 wherein the degree of LOI is measured by a ratio of the level of expression due to the allele which is normally imprinted, to the sum of the level of expression due to the allele which is normally imprinted and the level of expression due to the allele which is normally expressed.

15. The method of claim 14 wherein partial LOI is within a range of 50% to 99.9% or less than a 3:1 ratio of a more abundant allele to a less abundant allele.

16. The method of claim 15 wherein the degree of LOI is measured by the formula comprising:

$$\frac{E_i}{E_i + E_n} \times 100 \times 2$$

wherein $E_i$ is the level of expression due to the allele which is normally imprinted, and $E_n$ is the level of expression due to the allele which is normally expressed.

17. The method of claim 9, wherein the disease is cancer, SIDS, mental retardation, obesity, gross motor disturbances, diabetes, or gestational diabetes.

18. The method of claim 17, comprising measuring the degree of LOI for at least one gene in said normal biological sample.

19. The method of claim 18 wherein the degree of LOI is measured by a ratio of the level of expression due to the allele which is normally imprinted, to the sum of the level of expression due to the allele which is normally imprinted and the level of expression due to the allele which is normally expressed.

20. The method of claim 19 wherein partial LOI is within a range of 50% to 99.9% or less than a 3.1 ratio of a more abundant allele to a less abundant allele.

* * * * *

UNITED STATES PATENT AND TRADEMARK OFFICE
CERTIFICATE OF CORRECTION

PATENT NO. : 6,235,474 B1
DATED : May 22, 2001
INVENTOR(S) : Andrew P. Feinberg

It is certified that error appears in the above-identified patent and that said Letters Patent is hereby corrected as shown below:

Column 31, claim 10,
Line 39, "9" has been replace with -- 17 --.

Column 32, claim 11,
Line 1, "10" has been replace with -- 17 --.

Signed and Sealed this

Eighth Day of January, 2002

Attest:

JAMES E. ROGAN
Attesting Officer   Director of the United States Patent and Trademark Office

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
atcgttgagg agtgctgttt c                                              21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
cttggacttt gagtcaaatt gg                                             22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
ggtcgtgcca attacatttc a                                              21
```

```
<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ctcatacttt atgcatcccc g                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
cggggatgca taaagtatga g                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gcctgatcca tacagatatc g                                              21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gcatctctgt catggtggaa ag                                             22

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide Probe

<400> SEQUENCE: 8
tgtgatttct ggggtccttc ttttctctt                                      29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide Probe

<400> SEQUENCE: 9
tgtgatttct ggggcccttc ttttctctt                                      29
```